US009801874B2

(12) United States Patent
Monte et al.

(10) Patent No.: US 9,801,874 B2
(45) Date of Patent: Oct. 31, 2017

(54) METHOD FOR THE PREPARATION OF LIPOSOME ENCAPSULATED VINCRISTINE FOR THERAPEUTIC USE

(71) Applicants: Spectrum Pharmaceuticals, Inc., Henderson, NV (US); Tekmira Pharmaceuticals Corporation, Burnaby (CA)

(72) Inventors: William T. Monte, Lincolnshire, IL (US); Christopher James Barbosa, Coquitlam (CA); Thomas Philip Weber, Surrey (CA)

(73) Assignees: Spectrum Pharmaceuticals, Henderson, NV (US); Tekmira Pharmaceuticals Corporation, Burnaby (CA)

( * ) Notice: Subject to any disclaimer, the term of this patent is extended or adjusted under 35 U.S.C. 154(b) by 0 days.

(21) Appl. No.: 14/646,359

(22) PCT Filed: Nov. 20, 2013

(86) PCT No.: PCT/US2013/071096
§ 371 (c)(1),
(2) Date: May 20, 2015

(87) PCT Pub. No.: WO2014/081887
PCT Pub. Date: May 30, 2014

(65) Prior Publication Data
US 2015/0290184 A1 Oct. 15, 2015

Related U.S. Application Data

(60) Provisional application No. 61/728,378, filed on Nov. 20, 2012.

(51) Int. Cl.
*A61K 31/475* (2006.01)
*A61K 9/127* (2006.01)

(52) U.S. Cl.
CPC ............ *A61K 31/475* (2013.01); *A61K 9/127* (2013.01); *A61K 9/1272* (2013.01); *A61K 9/1278* (2013.01)

(58) Field of Classification Search
None
See application file for complete search history.

(56) References Cited

U.S. PATENT DOCUMENTS

| | | | |
|---|---|---|---|
| 2,932,718 A * | 4/1960 | Marsters | B01L 7/00 219/242 |
| 4,186,183 A | 1/1980 | Steck et al. | |
| 4,217,344 A | 8/1980 | Vanlerberghe et al. | |
| 4,235,871 A | 11/1980 | Papahadjopoulos et al. | |
| 4,261,975 A | 4/1981 | Fullerton et al. | |
| 4,485,054 A | 11/1984 | Mezei et al. | |
| 4,501,728 A | 2/1985 | Geho et al. | |
| 4,603,044 A | 7/1986 | Geho et al. | |
| 4,737,323 A | 4/1988 | Martin et al. | |
| 4,774,085 A | 9/1988 | Fidler | |
| 4,837,028 A | 6/1989 | Allen | |
| 4,885,172 A | 12/1989 | Bally et al. | |
| 4,906,476 A | 3/1990 | Radhakrishnan | |
| 4,920,016 A | 4/1990 | Allen et al. | |
| 4,946,787 A | 8/1990 | Eppstein et al. | |
| 4,952,408 A | 8/1990 | Rahman | |
| 4,957,773 A | 9/1990 | Spencer et al. | |
| 4,971,802 A | 11/1990 | Tarcsay et al. | |
| 5,023,087 A | 6/1991 | Yau-Young | |
| 5,059,421 A | 10/1991 | Loughrey et al. | |
| 5,077,056 A | 12/1991 | Bally et al. | |
| 5,165,922 A | 11/1992 | Hellstrom et al. | |
| 5,171,578 A | 12/1992 | Bally et al. | |
| 5,192,549 A | 3/1993 | Barenolz et al. | |
| 5,262,168 A | 11/1993 | Lenk et al. | |
| 5,417,978 A | 5/1995 | Tari et al. | |
| 5,534,499 A | 7/1996 | Ansell | |
| 5,543,152 A | 8/1996 | Webb et al. | |
| 5,552,154 A | 9/1996 | Giovanella et al. | |
| 5,552,156 A | 9/1996 | Burke | |
| 5,567,592 A | 10/1996 | Benet et al. | |
| 5,595,756 A | 1/1997 | Bally et al. | |
| 5,648,090 A | 7/1997 | Rahman et al. | |
| 5,714,163 A | 2/1998 | Forssen et al. | |
| 5,736,155 A | 4/1998 | Bally et al. | |
| 5,741,516 A | 4/1998 | Webb et al. | |
| 5,755,788 A | 5/1998 | Strauss | |
| 5,762,957 A | 6/1998 | Mehlhorn | |

(Continued)

FOREIGN PATENT DOCUMENTS

| JP | 9-504517 | 5/1997 |
|---|---|---|
| JP | 2003-510239 A | 3/2003 |

(Continued)

OTHER PUBLICATIONS

Anonymous: Labeling Marqibo, FDA Website Reference ID 3172211, Internet Citation, Aug. 9, 2012, Retrieved from the Internet: URL:http://www.accessdata.fda.gov/drugsatfda_docs/label/2012/202497s000lbl.pdf (retrieved by WIPO on Mar. 10, 2014).
Puscalau Georgeta et al., Reliability of preparation procedure for sphingosomal vincristine. American Journal of Health-Systems Pharmacy, vol. 62, No. 15, pp. 1606-1612 (2005).
International Search Report and Written Opinion for International Application PCT/US2013/071096 filed on Nov. 20, 2013.
Grochow et al., Pharmacokinetics and pharmacodynamics of topotecan in patients with advanced cancer. Drug Metabolism and Disposition, vol. 20(5):706-713 (1992).
Gruner, Sol M., Materials properties of liposomal bilayers. Liposomes: From Biophysics to Therapeutics, Ostro, M.J. (Ed.), Marcel Dekker, New York, Chp. 1, pp. 1-38 (1987).

(Continued)

*Primary Examiner* — Celeste A Roney
(74) *Attorney, Agent, or Firm* — K&L Gates LLP; Louis C. Cullman; Hal Gibson

(57) ABSTRACT

Improved methods for efficiently constituting liposome encapsulated vincristine for intravenous injection (VSLI) with reduced risk of operational errors and contamination are disclosed.

15 Claims, 1 Drawing Sheet

(56) References Cited

U.S. PATENT DOCUMENTS

| | | | |
|---|---|---|---|
| 5,785,987 A | 7/1998 | Hope et al. |
| 5,814,335 A | 9/1998 | Webb et al. |
| 5,820,873 A | 10/1998 | Choi et al. |
| 5,837,282 A | 11/1998 | Fenske et al. |
| 5,885,613 A | 3/1999 | Holland et al. |
| 5,888,537 A | 3/1999 | Forssen et al. |
| 5,976,567 A | 11/1999 | Wheeler et al. |
| 6,056,973 A | 5/2000 | Allen et al. |
| 6,090,407 A | 7/2000 | Knight et al. |
| 6,110,491 A | 8/2000 | Kirprotin |
| 6,129,914 A | 10/2000 | Weiner et al. |
| 6,316,024 B1 | 11/2001 | Allen et al. |
| 6,320,017 B1 | 11/2001 | Ansell |
| 6,352,996 B1 | 3/2002 | Cao et al. |
| 6,355,268 B1 | 3/2002 | Slater et al. |
| 6,471,943 B1 | 10/2002 | Placke et al. |
| 6,548,071 B1 | 4/2003 | Chervian |
| 6,566,395 B1 | 5/2003 | Moran |
| 6,627,614 B1 | 9/2003 | Rubinfeld |
| 6,653,319 B1 | 11/2003 | Xiang et al. |
| 6,664,233 B1 | 12/2003 | Rubinfeld |
| 6,723,338 B1 | 4/2004 | Sarris et al. |
| 6,740,335 B1 | 5/2004 | Moynihan et al. |
| 6,825,206 B1 | 11/2004 | Gamcsik et al. |
| 6,855,331 B2 | 2/2005 | Vook et al. |
| 7,060,828 B2 | 6/2006 | Madden et al. |
| 7,094,423 B1 | 8/2006 | Maurer et al. |
| 7,244,448 B2 | 7/2007 | Madden et al. |
| 7,244,450 B2 | 7/2007 | Sarris et al. |
| 7,247,316 B2 | 7/2007 | Sarris et al. |
| 7,311,924 B2 | 12/2007 | Sarris et al. |
| 7,452,550 B2 | 11/2008 | Madden et al. |
| 7,811,602 B2 | 10/2010 | Cullis et al. |
| 7,887,836 B2 | 2/2011 | Sarris et al. |
| 2001/0016196 A1 | 8/2001 | Benz et al. |
| 2003/0091621 A1 | 5/2003 | Tardi et al. |
| 2003/0147945 A1 | 8/2003 | Tardi et al. |
| 2003/0219476 A1 | 11/2003 | Ahmad et al. |
| 2004/0071768 A1 | 4/2004 | Sarris et al. |
| 2004/0170678 A1 | 9/2004 | Madden et al. |
| 2004/0171768 A1 | 9/2004 | Miho |
| 2005/0118250 A1 | 6/2005 | Tardi et al. |
| 2005/0129750 A1 | 6/2005 | Hu et al. |
| 2006/0008535 A1 | 1/2006 | Sabin |
| 2006/0008909 A1 | 1/2006 | Cullis et al. |
| 2006/0093662 A1 | 5/2006 | Madden et al. |
| 2006/0222694 A1 | 10/2006 | Oh et al. |
| 2006/0257465 A1 | 11/2006 | Maurer et al. |
| 2006/0269594 A1 | 11/2006 | Madden et al. |
| 2007/0292322 A1* | 12/2007 | Soung et al. ................ 422/198 |
| 2009/0028933 A1 | 1/2009 | Thomas |
| 2009/0285878 A1 | 11/2009 | Hope et al. |
| 2011/0086826 A1 | 4/2011 | Madden et al. |
| 2012/0003297 A1 | 1/2012 | Sarris et al. |
| 2012/0164211 A1 | 6/2012 | Thomas |
| 2013/0136787 A1 | 5/2013 | Madden et al. |

FOREIGN PATENT DOCUMENTS

| | | | |
|---|---|---|---|
| JP | 2004-501955 A | | 1/2004 |
| JP | 2004-277374 | | 10/2004 |
| WO | 88/04924 A1 | | 7/1988 |
| WO | 88/06442 A1 | | 9/1988 |
| WO | 89/11292 A1 | | 11/1989 |
| WO | 90/14105 A1 | | 11/1990 |
| WO | 91/04019 A1 | | 4/1991 |
| WO | 91/17424 A1 | | 11/1991 |
| WO | 94/20145 A1 | | 9/1994 |
| WO | 95/08986 A1 | | 4/1995 |
| WO | 95/35094 A1 | | 12/1995 |
| WO | 96/00057 A1 | | 1/1996 |
| WO | 98/17256 A1 | | 4/1998 |
| WO | 99/13816 A2 | | 3/1999 |
| WO | 99/51202 A2 | | 10/1999 |
| WO | WO 00-59473 | * | 3/2000 |
| WO | 00/23052 A1 | | 4/2000 |
| WO | 00/59473 A1 | | 10/2000 |
| WO | 02/02077 A2 | | 1/2002 |
| WO | 02/02078 A2 | | 1/2002 |
| WO | 2004/017940 A2 | | 3/2004 |
| WO | 2005/002546 A1 | | 1/2005 |
| WO | 2005/107712 A1 | | 11/2005 |
| WO | 2006/052767 A2 | | 5/2006 |
| WO | 2014/081887 A1 | | 5/2014 |

OTHER PUBLICATIONS

Guo et al., Determination by liquid chromatography with fluorescence detection of total 7-ethyl-10-hydroxy-camptothecin (SN-38) in beagle dog plasma after intravenous administration of liposome-based SN-38 (LE-SN38). Journal of Chromatography B, vol. 791:85-92 (2003).

Haas et al., Strong antitumor efficacy of a cationic liposomal camptothecin formulation (LipoCamTM) in the subcutaneous human melanoma. Proceedings of the American Association for Cancer Research, vol. 44(2nd ed.):350-351, Abstract No. R1793 (2003).

Haim et al., Full dose vincristine (without 2-mg Dose Limit) in the treatment of lymphomas. Cancer, vol. 73 (10):2515-2519 (1994).

Hardman et al., Efficacy of treatment of colon, lung and breast human carcinoma xenografts with: Doxorubicin, cisplatin, irinotecan or topotecan. Anticancer Research, vol. 19:2269-2274 (1999).

Hatefi et al., Review: Camptothecin delivery methods. Pharmaceutical Research, vol. 19(10):1389-1399 (2002).

Heath, T., Covalent attachment of proteins to lipsomes. Methods in Enzymology, 149:111-119 (1987).

Heath et al., Covalent attachment of immunoglobulins to liposomes via glycosphingolipids. Biochimica et Biophysica Acta, vol. 640:68-81 (1981).

Hope et al., Generation of multilamellar and unilamellar phospholipid vesicles. Chemistry and Physics of Lipids, vol. 10:89-107 (1986).

Hope et al., Production of large unilamellar vesicles by a rapid extrusion procedure. Characterization of size distribution, trapped volume and ability to maintain a membrane potential. Biochim. Et Biophys. Acta 812:55-65 (1985).

Hsiang et al., Identification of mammalian DNA topoisomerase I as an intracellular target or the anticancer drug camptothecin. Cancer Research, vol. 48:1722-1726 (1988).

Hudson et al., Xenotransplantation of human lymphoid malignancies is optimized in mice with multiple immunologic defects. Leukemia, 12(12):2029-2033 (1998).

International Preliminary Report on Patentability for Application No. PCT/US2005/040061, dated Jun. 26, 2007.

International Search Report for Application No. PCT/CA01/00981 dated Aug. 29, 2002.

International Preliminary Examination Report Application No. PCT/CA01/00981 dated Nov. 22, 2002.

International Search Report for Application No. PCT/CA01/00925 dated Aug. 29, 2002.

International Preliminary Examination Report for Application No. PCT/CA01/00925 dated Nov. 22, 2002.

International Search Report for Application No. PCT/US2005/040061 dated May 30, 2007.

International Search Report for Application No. PCT/US00/08669 dated Jul. 9, 2000.

International Search Report for Application No. PCT/US2005/028233 dated Jan. 5, 2006.

Preliminary Report on Patentability for Application No. PCT/US2005/028233 dated Feb. 13, 2007.

Written opinion for Application No. PCT/US20051028233 dated Jan. 2006.

Jackson et al., Intravenous vincristine infusion: phase I trial. Cancer, vol. 48:2559-2564 (1981).

Jackson et al., Treatment of advanced non-hodgkin's lymphoma with vincristine infusion. Cancer, vol. 53:2601-2606 (1984).

(56) References Cited

OTHER PUBLICATIONS

Kamath et al., Therapeutic efficacy of liposome-based formulation of SN38 against leukemia model in CD2F1 mice. Proceedings of the American Association for Cancer Research, vol. 44, 2nd Ed., Abstract No. 1784 (2003).
Kantarjian et al., Acute lymphocytic leukaemia in the elderly: characteristics and outcome with the vincristine-adriamycin-dexamethasone (VAD) regimen. Br. J. Haematol., vol. 88(1):94-100 (1994).
Kantarjian et al., Experience with vincristine, doxorubicin, and dexamethasone (VAD) chemotherapy in adults with refractory acute lymphocytic leukemia. Cancer, vol. 64:16-22 (1989).
Kearney et al., Preformulation studies to aid in the development of a ready-to-use injectable solution of the antitumor agent, topotecan. International Journal of Pharmaceutics, vol. 127:229-237 (1996).
Khan et al., Liposome based formulation of SN-38 (LE-SN38): A four-cycle toxicity evaluation in beagle dogs. Toxicological Sciences, vol. 72(S-1):386, Abstract No. 1873 (2003).
Khan et al., A sensitive and rapid liquid chromatography tandem mass spectometry method for quantitative determination of 7-ethyl-10-hydroxycamptothecin (SN-38) in human plasma containing liposome-based SN-38 (LE-SN38). Biomedical Chromatography, vol. 17:493-499 (2003).
King R.E., Remington's Pharmaceutical Sciences, 17th Ed., Mack Publishing Co., Philadelphia, PA, Part 8, Pharmaceutical Preparations and Their Manufacture, pp. 1409-1677 (1985).
Kluin-Nelemans et al., A new non-Hodgkin's B-cell line (DoHH2) with a chromosomal translocation t(14;18) (q32; q21). Leukemia, 5(3):221-224 (1991).
Knight et al., 9-Nitrocamptothecin liposome aerosol treatment of human cancer subcutaneous xenografts and pulmonary cancer metastases in mice. Ann. N.Y. Acad. Sci., vol. 922:151-163 (2000).
Knight et al., Anti-Cancer activity of 9-Nitrocamptothecin liposome aerosol in mice. Transactions of the American and Climatological Association, vol. 111:135-145 (2000).
Knight et al., Anticancer exffect of 9-nitrocamptothecin liposome aerosol on human cancer xenografts in nude mice. Cancer Chemother. Pharmacol., vol. 44:177-186 (1999).
Koshkina et al., Pharmacokinetics and tissue distribution of camptothecin after delivery as a liposome aerosol or following intramuscular injection in mice. Proceedings of the American Association for Cancer Research, vol. 40:110-111, Abstract No. 734 (1999).
Koshkina et al., 9-Nitrocamptothecin liposome aerosol treatment of melanoma and osteosarcoma lung metastases in mice. Clinical Cancer Research, vol. 6:2876-2880 (2000).
Koshkina et al., Distribution of camptothecin after delivery as a liposome aerosol or following intramuscular injection in mice. Cancer Chemother. Pharmacol., vol. 44:187-192 (1999).
Koshkina et al., Improved respiratory delivery of the anticancer drugs, camptothecin and paclitaxel, with 5% C02-enriched air: pharmacokinetic studies. Cancer Chemother. Pharmacol., vol. 47:451-456 (2001).
Kruszewski et al., Comparison of the human blood chemistry of free versus liposomal forms of the clinically-relevant topoisomerase I inhibitor Lurtotecan (GI147221). Proceedings of the American Association for Cancer Research, vol. 41:324, Abstract No. 2056 (2000).
Lei et al., Enhanced therapeutic efficacy of a novel liposome-based formulation of SN-38 against human tumor models in SCID mice. Anti-Cancer Drugs, vol. 15:773-778 (2004).
Leonetti et al., Antibody-targeted liposomes containing oligodeoxyribonucleotides complementary to viral RNA selectively inhibit viral replication. Proc. Natl. Acad. Sci. USA 87:2448-2451 (1990).
Lerchen, Hans-Georg, Camptothecin antitumor agents. IDrugs, vol. 2(9):896-906 (1999).
Liu et al., Simple and efficient liposomal encapsulation of topotecan by ammonium sulfate gradient: stability, pharmacokinetic and therapeutic evaluation. Anti-Cancer Drugs, vol. 13:709-717 (2002).
Liu et al., A versatile prodrug approach for liposomal core-loading of water-insoluble camptothecin anticancer drugs. J. Am. Chem. Soc., vol. 124(26):7650-7651 (2002).
Loos et al., Clinical pharmacodynamics of liposomal lurtotecan (NX 211 ): Urinary excretion predicts hematologic toxicity. Proceedings of the American Association for Cancer Research, vol. 42:102, Abstract No. 551 (2001).
Loos et al., Liposomal lurtotecan (NX211 ): determination of total drug levels in human plasma and urine by reversed-phase high-performance liquid chromatography. Journal of Chromatography B, vol. 738:155-163 (2000).
Loos et al., Structural identification and biological activity of 7-methyl-10, 11-ethylenedioxy-20(S)-camptothecin, a photodegradant of lurtotecan. Clinical Cancer Research, vol. 8:856-862 (2002).
Lopez-Barcons et al., The novel highly lipophilic topoisomerase I inhibitor DB67 is effective in the treatment of liver metastases of murine CT-26 colorectal carcinoma. Proceedings of the American Association for Cancer Research, vol. 44(2):348, Abstract No. 1782 (2003).
Stewart et al., Cyclophosphamide, doxorubicin, vincristine, and dexamethasone in primay lymphoma of the brain: a case report. Cancer Treatment Reports, 67(3), pp. 287-291 (1983).
Subramanian et al., Liposomal encapsulation increases the activity of the topoisomerase I inhibitor topotecan. Oncology Research, 7(9):461-469 (1995).
Sugarman et al., Liposomal camptothecin: formulation and cytotoxicity against KB cells. Proceedings of the American Association for Cancer Research, vol. 34:422, Abstract No. 2519 (1993).
Szoka et al., Comparative properties and methods of preparation of lipid vesicles (liposomes). Ann. Rev. Biophys. Bioeng., vol. 9:467-508 (1980).
Tanyeli et al., Formulation and pharmacological characterization of the novel polyamine camptothecin CT-17 encapsulated in low-clearance liposomes. Proceedings of the American Association for Cancer Research, vol. 42:255-256, Abstract No. 1379 (2001).
Tardi et al., Liposomal encapsulation of topotecan enhances anticancer efficacy in murine and human xenograft models. Cancer Research, vol. 60:3389-3393 (2000).
The Merck Index, Eleventh Edition, Entry Nos. 9887 Vinblastine, 9891 Vincristine, and 9893 Vindoline. Merck & Co., Inc. Rahway, New Jersey, Susan Budavari (Ed.) pp. 1570-1571 (1989).
Thomas et al., Phase 1 multicenter study of vincristine sulfate liposomes injection and dexamethasone in adults with relapsed or refractory acute lymphoblastic leukemia. Cancer, vol. 115(23):5490-5498 (2009).
Thomas, DA et al., Phase II study of liposomal vincristine (Lipov) in relapsed or refractory adult acute lymphoblastic leukemia (ALL). Blood, vol. 94(10, Supp. 1 part 1 of 2):238b, Abstract No. 4269 (1999).
Thompson et al., Animal models for studying the action of topoisomerase I targeted drugs. Biochimica et Biophysica Acta, vol. 1400:301-319 (1998).
Tomkinson et al., In vivo Evaluation of NX 211 in combination with cisplatin, 5-FU and paclitaxel. Proceedings of the American Association for Cancer Research, vol. 41:144, Abstract No. 917 (2000).
Tomkinson et al., Efficacy of NX 211 in SCID mouse models of human leukemia. Proceedings of the American Association for Cancer Research, vol. 42:100, Abstract No. 542 (2001).
Tomkinson et al., OSI-211, a novel liposomal topoisomerase I inhibitor, is active in SCID mouse models of human AML and ALL. Leukemia Research, vol. 27:1039-1050 (2003).
Trosko et al., Mechanism of up-regulatd gap junctional intercellular communication during chemoprevention and ahemotherapy of cancer. Mutation Research, 480-481:219-229 (2001).
Ulukan et al., Controlled release of topotecan from thermosensitive liposomes. Proceedings of the American Association for Cancer Research, vol. 36:308, Abstract No. 1833 (1995).
U.S. Appl. No. 08/316,394, filed Sep. 30, 1984.
U.S. Appl. No. 08/481,120, filed Jun. 7, 1995.
U.S. Appl. No. 08/996,783, filed Dec. 23, 1997.
U.S. Appl. No. 11/659,754, filed Feb. 7, 2007.
U.S. Appl. No. 11/880,472, filed Jul. 20, 2007.

(56) References Cited

OTHER PUBLICATIONS

U.S. Appl. No. 60/264,616 entitled, Liposomal antineoplastic drugs and uses thereof, Madden, Thomas D. et al. (2001).
U.S. Appl. No. 60/215,556 entitled, Improved liposomal camptothecins and uses thereof, Madden, Thomas D. et al. (2001).
Verschraegen et al., Alternate administration of camptothecin analogues. Ann. N.Y. Acad. Sci., vol. 922:237-246 (2000).
Verschraegen et al., Feasibility, phase I, and pharmacological study of aerosolized liposomal 9-Nitro-20(S)-Camptothecin in patients with advanced malignancies in the lungs. Ann. N.Y. Acad. Sci., vol. 922:352-354 (2000).
Verschraegen et al., Clinical evaluation of the delivery and safety of aerosolized liposomal 9-Nitro-20(S)-Camptothecin in patients with advanced pulmonary malignancies. Clinical Cancer Research, vol. 10:2319-2326 (2004).
Wall et al., Plant antitumor agents. I. The isolation and structure of camptothecin, a novel alkaloidal leukemia and tumor inhibitor from Camptotheca acuminata. J. Am. Chem. Soc., vol. 88(16):3888-3890 (1966).
Waud, Ph.D., William R., Murine L1210 and P388 Leukemias. Anticancer Drug Development Guide: Preclinical Screening, Clinical Trials, and Approval, B. Teicher (Ed.), Humana Press Inc., Totowa, NJ, Chp. 4, pp. 59-74 (1997).
Webb et al., Sphingomyelin-cholesterol liposomes significantly enhance the pharmacokinetic and therapeutic properties of vincristine in murine and human tumour models. British Journal of Cancer, vol. 72:896-904 (1995).
Weeratne et al., Toxicity of sphingomyelin-containing liposomes after chronic injection into mice. Br. J. Exp. Path., vol. 64:670-676 (1983).
Williams et al., Low density lipoprotein receptor-independent hepatic uptake of a synthetic, cholesterol-scavenging lipoprotein: implications for the treatment of receptor-deficient atherosclerosis. Proc. Natl. Acad. Sci. USA 85:242-246 (1988).
Wozniak et al., Randomized trial comparing cisplatin plus vinorelbine in the treatment of advanced non-small cell lung cancer: a southwest oncology group study. J. Clin. Oncol. 16(7):2459-2465, 1998.
Yu et al., Stealth liposome formulation enhances antitumor efficacy of CKD-602, a topoisomerase I inhibitor, in human tumor xenograft models. Proc. Amer. Assoc. Cancer Res., vol. 45:710, Abstract No. 3069 (2004).
Zhang et al., Development and characterization of a novel liposome-based formulation of SN-38. International Journal of Pharmaceutics, vol. 270:93-107 (2004).
Zhang et al., A method for determining the encapsulation ratio of camptothecin in polyphase liposome and studies on its leakage property. Acta Pharmaceutica Sinica, vol. 22(12):912-922 (1987).
Zufia et al., Separation methods for camptothecin and related compounds. Journal of Chromatography B, vol. 764:141-159 (2001).
Zunino et al., Camptothecins in clinical development. Expert Opin. Investig. Drugs, vol. 13(3):269-284 (2004).
Zunino et al., Current status and perspectives in the development of camptothecins. Current Pharmaceutical Design, vol. 8:2505-2520 (2002).
Abraham et al., An evaluation of transmembrane ion gradient-mediated encapsulation of topotecan within liposomes. Journal of Controlled Release, vol. 96:449-461 (2004).
Alekseevak, et al., Use of dexamethasone in treatment of high- and low-grade non-Hodgkin's lymphoma. Vopr. Onkol., vol. 50(6):726-728 (2004).
Allen et al., Chronic liposome administration in mice: Effects on reticuloendothelial function and tissue distribution. The Journal of Pharmacology and Experimental Therapeutics, vol. 229(1):267-275 (1984).
Allen et al., Large unilamellar liposomes with low uptake into the reticuloendothelial system. FEBS Letters, vol. 223(1):42-46 (1987).
Allen et al., Liposomes containing synthetic lipid derivatives of poly(ethylene glycol) show prolonged circulation half-lives in vivo. Biochimica et Biophysica Acta, vol. 1066:29-36 (1991).
Allen et al., Liver pathology accompanying chronic liposome administration in mouse. Research Communications in Chemical Pathology and Pharmacology, vol. 50(2):281-290 (1985).
Allen et al., Pharmacokinetics of stealth versus conventional liposomes: effect of dose. Biochimica et Biophysica Acta, vol. 1068:133-141 (1991).
Allen et al., Subcutaneous administration of liposomes: a comparison with the intravenous and intraperitoneal routes of injection. Biochimica et Biophysica Acta, vol. 1150(1):9-16 (1993).
Allen et al., Liposomes with prolonged circulation times: factors affecting uptake by reticuloendothelial and other tissues. Biochimica et Biophysica Acta, vol. 981:27-35 (1989).
Apostolidou et al., Phase I study of OSI-211, a novel liposomal topoisomerase 1 (Topo 1) inhibitor, in patients with refractory leukemia. Blood, Abstract No. 4575 (2002).
Bedikian et al., A pilot study with vincristine sulfate liposome infusion in patients with metastatic melanoma. Melanoma Research, vol. 18(6), pp. 400-404 (2008).
Begu et al., Spectrofluorimetry study of interaction of camptothecin with liposomal bilayer. Luminescence, vol. 15:78-79 (Abstract) (2000).
Belgaumi et al., Dexamethasone-associated toxicity during induction chemotherapy for childhood acute lymphoblastic leukemia is augmented by concurrent use of danunomycin. Cancer 97(11), pp. 2898-2903, 2003.
Bell et al., Topoisomerase I (Topo-1) modulation by liposomal GI147211 (NX211 ). Proc. Amer. Assoc. Cancer Res., vol. 41:773, Abstract No. 4915 (2000).
Bevins et al., Tumor cell cycle disruption and apoptosis induced by DB-67, a highly lipophilic camptothecin displaying improved human blood stability. Proceedings of the American Association for Cancer Research, vol. 42:102, Abstract No. 554 (2001).
Biloti et al., Lipid membrane with low proton permeability. Biochimica et Biophysica Acta, vol. 1611:1-4 (2003).
Bloomfield, V., Quasi-elastic light scattering application in biochemistry and biology. Ann. Rev. Biophys. Bioeng. 10:421-450, 1981.
Bom et al., The highly lipophilic DNA topoisomerase I inhibitor DB-67 displays elevated lactone levels in human blood and potent anticancer activity. Journal of Controlled Release, vol. 74:325-333 (2001).
Bom et al., The structural basis of camptothecin loading and retention in liposomal drug carriers. Proceedings of the American Association for Cancer Research, vol. 42:374, Abstract No. 2016 (2001).
Bom et al., The novel silatecan 7-tert-butyldimethylsilyl-10-hydroxycamptothecin displays high lipophilicity, improved human blood stability, and potent anticancer activity. J. Med. Chem., vol. 43:3970-3980 (2000).
Boman et al., Liposomal vincristine which exhibits increased drug retention and increased circulation longevity cures mice bearing P388 tumors. Cancer Research, vol. 54:2830-2833 (1994).
Boman et al., Vincristine-induced dermal toxicity is significantly reduced when the drug is given in liposomes. Cancer Chemother. Pharmacol., vol. 37:351-355 (1996).
Bostrom et al., Dexamethasone versus prednisone and daily oral versus weekly intravenous mercaptopurine for patients with standard-risk acute lymphoblastic leukemia: a report from the Children's Cancer Group. Blood, vol. 101 (10):3809-3817 (2003).
Burke et al., Development and evaluation of a liposomal formulation of highly lipophilic 7-t-butyldimethylsily-1-10-hydroxy-camptothecin. Proceedings of the American Association for Cancer Research, vol. 40:113, Abstract No. 752 (1999).
Burke, T.G. et al., "Enhanced Bloodstream Stability and In Vivo Activity of Topotecan Formulated in Liposomes," Pharm. Res., vol. 11(10):S-323, Abstract No. POD 7596 (1994).
Burke et al., Liposomal stabilization of camptothecins. Proceedings of the American Association for Cancer Research, vol. 35:416, Abstract No. 2479 (1994).

(56) References Cited

OTHER PUBLICATIONS

Burke et al., A versatile pro-drug approach for the liposomal core loading of camptothecin anticancer drugs. Proceedings of the American Association for Cancer Research, vol. 43:1156, Abstract No. 5731 (2002).
Burke et al., Camptothecin design and delivery approaches for elevating anti-topoisomerase I Activities in vivo. Ann. N.Y. Acad. Sci., vol. 922:36-45 (2000).
Burke et al., Liposomal formulations of camptothecins for cancer treatment. Abstracts of Papers American Chemical Society, In Proceedings of the 208th ACS National Meeting, Abstract No. 50 (1994).
Burke et al., Liposomal stabilization of camptothecin's lactone ring. J. Am. Chem. Soc., vol. 114:8318-8319 (1992).
Burke et al., Liposomal stabilization of the lactone ring of camptothecin anticancer drugs. Pharm. Res., vol. 11(10): S220, Abstract No. PDD 7183 (1994).
Burke et al., Stabilization of topotecan in low pH liposomes composed of distearoylphosphatidylcholine. Journal of Pharmaceutical Sciences, vol. 83(7):967-969 (1994).
Lundberg, Bo. B., Biologically active camptothecin derivatives for incorporation into liposome bilayers and lipid emulsions. Anti-Cancer Drug Design, vol. 13:453-461 (1998).
Luo et al., Studies on polyphase liposome of camptothecin, PL-CSA. Yao xue xue bao, Acta Pharmaceutica Sinica, vol. 19(1):63-68 (1984). (full Chinese article and English abstract.
Lynam et al., Camptothecin analogue efficacy in vitro: Effect of liposomal encapsulation of GI147211C (Lurtotecan) on in vitro cytotoxicity for multiple tumor cell types. Proceedings of the American Association for Cancer Research, vol. 39: 421, Poster No. 2863 (1998) (2 pages).
Lynam et al., Camptothecin analogue efficacy in vitro: Effect of liposomal encapsulation of GI147211C (NX211). Drug Delivery, vol. 6:51-62 (1999).
Mackenzie et al., A phase I study of OSI-211 and cisplatin as intravenous infusions given on days 1, 2 and 3 every 3 weeks in patients with solid cancers. Annals of Oncology, vol. 15:665-670 (2004).
Madden et al., Encapsulation of topotecan in lipid-based carrier systems. Evaluation of drug stability and plasma elimination in a murine model, and comparison of antitumor efficacy against murine L1210 and B16 Tumors. Proceedings of ASCO, vol. 17:196a, Abstract No. 754 (1998).
Madden et al., The accumulation of drugs within large unilamellar vesicles exhibiting a proton gradient: a survey. Chemistry and Physics of Lipids, vol. 53:37-46 (1990).
Maliepaard et al., Circumvention of breast cancer resistance protein (BCRP)- mediated resistance to camptothecins in vitro using non-substrate drugs or the BCRP inhibitor GF120918. Clinical Cancer Research, vol. 7:935-941 (2001).
Mamot et al., Liposome-based approaches to overcome anticancer drug resistance. Drug Resistance Updates, vol. 6:271-279 (2003).
Mayer et al., Solute distributions and trapping efficiencies observed in freeze-thawed multilamellar vesicles. Biochimica et Biophysica Acta, vol. 817:193-196 (1985).
Mayer et al., Characterization of liposomal systems containing doxorubicin entrapped in response to pH gradients. Biochimica et Biophysica Acta, vol. 1025:143-151 (1990).
Mayer et al., Liposomal vincristine preparations which exhibit decreased drug toxicity and increased activity against murine L1210 and P388 Tumors. Cancer Research, vol. 50:575-579 (1990).
Mayer et al., Identification of vesicle properties that enhance the antitumor activity of liposomal vincristine against murine L1210 leukemia. Cancer Chemother. Pharmacol., vol. 33:17-24 (1993).
Mayer et al., Vesicles of variable sizes produced by a rapid extrusion procedure. Biochim. Et Biophys. Acta 858:161-168 (1986).
Mayer et al., Techniques for encapsulating bioactive agents into liposomes. Chem. and Phys. of Lipids 40:333-345 (1986).

McCabe et al., Comparative activity of oral and parenteral topotecan in murine tumor models: Efficacy of oral topotecan. Cancer Investigation, vol. 12(3):308-313 (1994).
Meerum et al., Clinical pharmacology of anticancer agents in relation to formulations and administration routes. Cancer Treatment Reviews, vol. 25:83-101 (1999).
Messerer et al., Liposomal irinotecan: Formulation development and therapeutic assessment in murine xenograft models of colorectal cancer. Clinical Cancer Research, vol. 10:6638-6649 (2004).
Michaelis et al., Cationic liposomes (catioms) to target tumor neovasculature. Abstracts of Papers, American Chemical Society, in Proceedings of the 226th ASC National Meeting, Abstract No. 2 (2003).
Mi et al., Differential interactions of camptothecin lactone and carboxylate forms with human blood components. Biochemistry, vol. 33:10325-10336 (1994).
Nyholm et al., Properties of palmitoyl phosphatidylcholine, sphingomyelin, and dihydrosphingomyelin bilayer membranes as reported by different fluorescent reporter molecules. Biophysical Journal, vol. 84:987-997 (2003).
O'Brien et al., A phase 2 study to evaluate the safety and efficacy of weekly doses of Marqibo® (liposomal vincristine sulfate) in adult patients with Philadelphia Chromosome-Negative Acute Lymphoblastic Leukemia (Ph ALL) in second relapse or who progressed following two treatment lines. 52nd ASH Annual Meeting and Exposition, New Orleans, LA (2009).
O'Brien et al., Pivotal phase 2 study of weekly vincristine sulfate liposomes injection (VSLI, Marquibo®) in adults with philadephia chromosome-negative actue lymphoblastic leukemia (ALL) in second relapse or progressing following two anit-leukemia treatment lines. Blood, vol. 114, Issue 22, Abstract 3088 (2009).
O'Leary et al., Antiangiogenic effects of camptothecin analogues 9-Amino-20(S)-camptothecin, topotecan, and CPT-11 studied in the mouse cornea model. Clinical Cancer Research, vol. 5:181-187 (1999).
Ormrod et al., Topotecan. A Review of its efficacy in small cell lung cancer. Drugs, vol. 58(3):533-551 (1999).
Paciucci et al., Mitoxantrone, vincristine, and dexamethasone in pateints with refractory lymphoma. Am. J. Clin. Oncol. (CCT) 12(4), pp. 327-331 (1989).
Pal et al., Enhanced antitumor efficacy of liposome-based formulation of SN38 against human pancreatic tumor in SCID mice. Proceedings of the American Association for Cancer Research, Abstract No. 1785 (2003).
Parovichnikova, et al., Superhigh doses of dexamethasone in treatment of refractory forms of acute lymphoblast of adults. Ter. Arkh., vol. 75(7):21-23 (2003). Abstract only.
Plowman et al., Human tumor xenograft models in NCI drug development. Anticancer Drug Development Guide: Preclinical Screening, Clinical Trials, and Approval, B. Teicher (Ed.), Humana Press Inc., Totowa, N.J., Chpt. 6, pp. 101-125 (1997).
Poirot et al., Liposomal-camptothecin composed of cationic phospholipids containing unsturated fatty acids: Formulation and cytotoxicity studies. Proceedings of the American Association for Cancer Research, vol. 37:300, Abstract 2039 (1996).
Proulx et al., Incorporation of campthothecin into liposomes: a new approach for the treatment of leishmaniasis. Abstracts of the 39th Annual Interscience Conference on Antimicrobial Agents and Chemotherapy, pp. 730-731, Abstract No. 1856 (1999).
Proulx et al., Treatment of visceral leishmaniasis with sterically stabilized liposomes containing camptothecin. Antimicrobial Agents and Chemotherapy, vol. 45(9):2623-2627 (2001).
Quasthoff et al., Chemotherapy-induced peripheral neuropathy. J. Neurol., vol. 249:9-17 (2002).
Renneisen et al., Inhibition of expression of human immunodeficiency vivrus-1 in vitro by antibody-targeted liposomes containing antisense RNA to the env region. J. Biol. Chem. 265(27):16337-16342 (1990).
Rodriguez et al., Phase II study of sphingosomal vincristine in CHOP+/− Rituximab for patients with aggressive Non-Hodgkin's Lymphoma (NHL):Promising 3 Year follow-up results in elderly patients. Blood, vol. 106(11):277a, Poster Session 943 (2005).

(56) References Cited

OTHER PUBLICATIONS

Rodriguez et al., Sphingosomal vincristine in CHOP is a promising new treatment for elderly, as well as poor prognosis patients with aggressive non-Hodgkin's lymphoma (NHL): Follow-up results of a phase II study. Journal of Clinical Oncology, Proceedings of the 2004 ASCO Annual Meeting, vol. 22(14S) Poster Session 8080 (2004).

Rodriguez, M.A. et al., Vincristine Sulfate Liposomes Injection (Marqibo) in heavily pretreated patients with refractory aggressive non-hodgkin lymphoma. Cancer, vol. 115:3475-3482 (2009).

Sadzuka et al., Antitumor effect of CPT-11 encapsulated liposome and conversion to active metabolite. J. Liposome Res., pp. 101-102 (1998).

Sadzuka, Y., Effective prodrug liposome and conversion to active metabolite. Current Drug Metabolism, vol. 1:31-48 (2000).

Sadzuka et al., Effect of liposomalization on the antitumor activity, side-effects and tissue distribution of CPT-11. Cancer Letters, vol. 127:99-106 (1998).

Sadzuka et al., Effective irinotecan (CPT-11)-containing liposomes: Intraliposomal conversion to the active metabolite SN-38. Jpn. J. Cancer Res., vol. 90:226-232 (1999).

Sadzuka et al., The study of polyethyleneglycol-coated liposomes containing CPT-11. Journal of Liposome Research, vol. 7(2 &3):241-260 (1997).

Sarkar et al., Toxicity Evaluation of a liposome-based formulation of SN38 in mice. Toxicol. Sci., vol. 72 (S-1 ):83, Abstract No. 403 (2003).

Sarris et al., Liposomal vincristine in relapsed non-Hodgkin's lymphomas: Early results of an ongoing phase II trial. Annals of Oncology, vol. 11:69-72 (2000).

Saxon et al., Lipsomal anticancer drugs as agents to be used in combination with other anticancer agents: studies on a liposomal formulation with two encapsulated drugs. Journal of Liposome Research, 9(4), pp. 507-522 (1999) (Abstract only).

Schiffelers et al., In vivo synergistic interaction of liposome-coencapsulated gentamicin and ceftazidime. The Journal of Pharmacology and Experimental Therapeutics, 298(1), pp. 369-375, 2001.

Seiden et al., A phase II study of liposomal lurtotecan (OSI-211) in patients with topotecan resistant ovarian cancer. Gynecologic Oncology, vol. 93:229-232 (2004).

Semple et al., Comparative efficacy and therapeutic index of topotecan and liposomal topotecan in murine and human solid tumor models. Proceedings of the American Association for Cancer Research, vol. 44, Abstract No. 3658 (2003).

Semple et al., Pre-clinical evaluation of liposomal topotecan: increased efficacy and therapeutic index in murine and human xenograft tumor models compared to free drug. Proceedings of the American Association for Cancer Research. vol. 42:374, Abstract No. 2015 (2001).

Stano et al., Novel camptothecin analogue (Gimatecan)-containing liposomes prepared by the ethanol injection method. Journal of Liposome Research, vol. 14(1&2):87-109 (2004).

Burris III et al., Activity of topotecan a new topoisomerase I inhibitor, against human tumor colony-forming units in vitro. Journal of the National Cancer Institute, vol. 84(23):1816-1820 (1992).

Chavan et al., A comparative study of the human blood stability characteristics of remote-loaded liposomal carriers containing clinically-relevant camptothecins. Proc. Am. Assoc. Cancer Res., vol. 40:417 Abstract No. 2755 (1999).

Chen et al., Characterization of liposomal mimetic formulations for selective targeting. Proc. Amer. Assoc. Cancer Res., vol. 40:S-161, Abstract No. PT 6019 (1999).

Chen et al., Pharmacokinetic evaluation of liposomal camptothecin. Pharm. Res., vol. 13(9):S-479, Abstract No. PPDM 8345 (1996).

Cheung et al., Loading of doxorubicin into liposomes by forming $Mn^{2+}$-drug complexes. Biochimica et Biophysica Acta, vol. 1414:205-216 (1998).

Chien et al., Cytotoxicity evaluation of a liposome-based formulation of SN38 in human and murine cancer cell lines. Proc. Amer. Assoc. Cancer Res., vol. 44:314, Abstract No. 1607 (2003).

Choice et al., Delivery of topotecan using liposomes: Drug loading into liposomes and drug and carrier pharmacokinetics in female Balb/c mice. Proc. Amer. Assoc. Cancer Res., vol. 40:113, Abstract No. 753 (1999).

Chou et al., Effect of composition on the stability of liposomal Irinotecan prepared by a pH gradient method. Journal of Bioscience and Engineering, vol. 95(4):405-408 (2003).

Chow et al., Liposomal camptothecin and 9-Nitro-Camptothecin: Formulation, pharmacokinetics and preclinical anti-tumor activity. Proceed. Int'l. Syap. Control. Rel. Bioact. Mater., vol. 24:919-920 (1997).

Chow et al., Pharmacokinetics and in vivo antitumor activity of liposomal encapsulated camptothecin and its analog. Proceedings of the American Association for Cancer Research, vol. 38:258, Abstract No. 1733 (1997).

Chow et al., Modified lactone/carboxylate salt equilibria in vivo by liposomal delivery of 9-Nitro-Camptothecin. Ann. N.Y. Acad. Sci., vol. 922:164-174 (2000).

Clements et al., Antiangiogenic potential of camptothecin and topotecan. Cancer Chemother. Pharmacol., vol. 44:411-416 (1999).

Clements et al., Camptothecin exhibits selective cytotoxicity towards human breast carcinoma as compared to normal bovine endothelial cells in vitro.Anti-Cancer Drugs, vol. 7:851-857 (1996).

Colbern et al., Encapsulation of the topoisomerase I inhibitor GL147211C in pegylated (STEALTH) liposomes: Pharmacokinetics and antitumor activity in HT29 colon tumor xenografls. Clinical Cancer Research, vol. 4:3077-3082 (1998).

Corbett et al., In vivo methods for screening and preclinical testing, Use of rodent solid tumors for drug delivery. Anticancer Drug Development Guide: Preclinical Screening, Clinical Trials, and Approval, B. Teicher (Ed.), Humana Press, Totowa, N.J., Chapter 5, pp. 75-99 (1997).

Cortesi et al., Formulation study for the antitumor drug camptothecin: liposomes, micellar solutions and a microemulsion. International Journal of Pharmaceutics, vol. 159:95-103 (1997).

Cortesi et al., Liposomes, micelles and microemulsions as new delivery systems for camptothecin. Eur. J. Pharm. Sci., vol. 6(Suppl. 1):S3, Abstract No. 12 (1998).

Dallavalle et al., Perspectives in camptothecin development. Expert Opinion Ther. Patents, vol. 12 (6):837-844 (2002).

Daoud et al., Multilamellar liposomes as a delivery system for camptothecin (NSC 94600) and 9-aminocamptothecin (NSC 603071). Proceedings of the American Association for Cancer Research, vol. 34:367, Abstract No. 2188 (1993).

Daoud et al., Antitumor effect of liposome-incorporated camptothecin in human malignant xenografts. Anti-Cancer Drugs, vol. 6:83-93 (1995).

Deamer et al., Larger volume liposumes by an ether vaporization method. Biochim. Et Biophys. Acta 443:629-634 (1976).

Desjardins et al., Biodistribution of NX 211, Liposomal GI147211, in tumor bearing mice. Proceedings of the American Association for Cancer Research, vol. 41:702-703, Abstract No. 4467 (2000).

Desjardins et al., Biodistribution of NX211, liposomal lurtotecan, in tumor-bearing mice. Anti-Cancer Drugs, vol. 12:235-245 (2001).

Dumontet et al., Mechanisms of action of and resistance to antitubulin agents: microtubule dynamics, drug transport, and cell death. J. Clin. Onc., 17(3):1061-1070 (1999).

Dunton et al., New Options for the Treatment of Advanced Ovarian Cancer. Seminars in Oncology, vol. 24(1):Suppl. 5:SS-2-SS-11 (1997).

El-Kareh et al., Theoretical models for drug delivery to solid tumors. Critical Reviews in Biomedical Engineering, vol. 25(6):503-571 (1997).

Emerson et al., The topoisomerase I Inhibitor, NX211 demonstrates significant in vivo activity against human acute myeloid leukemia (AML) engrafted in SCID Mice. Blood, Abstract No. 4223 (1999).

Emerson et al., Enhanced in vivo antitumor efficacy of the liposome formulated topoisomerase I inhibitor lurtotecan. Proc. Amer. Assoc. Cancer Res., vol. 40:113, Abstract No. 751 (1999).

(56) References Cited

OTHER PUBLICATIONS

Emerson et al., In vivo antitumor efficacy of liposomal lurtotecan (NX211) in human xenografts. Proceedings of the American Association for Cancer Research, vol. 42:100-101, Abstract No. 545 (2001).

Emerson et al., NX-211, a liposomal formulation of lurtotecan demonstrates enhanced pharmacokinetic and antitumor activity. Proceedings of the American Association for Cancer Research, vol. 39:278, Abstract No. 1897 (1998).

Emerson et al., Antitumor efficacy, pharmacokinetics, and biodistribution of NX211: A low-clearance liposomal formulation of lurtotecan. Clinical Cancer Research, vol. 6:2903-2912 (2000).

Emerson et al., In vivo antitumor activity of two new seven-substituted water-soluble camptothecin analogues. Cancer Research, vol. 55:603-609 (1995).

Emerson, David L., Liposomal delivery of camptothecins. Pharmaceutical Science and Technology Today, vol. 3 (6):205-209 (2000).

Erickson-Miller et al., Differential toxicity of camptothecin, topotecan and 9-aminocamptothecin to human, canine, and murine myeloid progenitors (CFU-GM) in vitro. Cancer Chemother. Pharmacol., vol. 39:467-472 (1997).

Fayad et al., Report of a phase II study of sphingosomal vincrsitine (SV) in patients with relapsed or refractory Hodgkin's disease. Journal of Clinical Oncology, vol. 23 (16S) Poster Session 6624 (2005).

Fenske et al., Ionophone-mediated uptake of ciprofloxacin and vincristine into large unilamellar vesicles exhibiting transmembrane ion gradients. Biochim. et. Biophys. Acta 1414:188-204, 1998.

Foley et al., The encephalopathy of chronic renal failure in children. Annals of Neurology, vol. 2(3):254 (1977).

Fraley et al., Entrapment of bacterial plasmid in phospholipid vesicles: potential for gene transfer. Proc. Natl. Acad. Sci. USA, 76(7):3348-3352 (1979).

Gabr et al., Cellular pharmacokinetics and cytotoxicity of camptothecin and topotecan at normal and acidic pHl. Cancer Research, vol. 57:4811-4816 (1997).

Garcia-Carbonero et al., Current perspectives on the clinical experience, pharmacology, and continued development of the camptothecins. Clinical Cancer Research, vol. 8:641-661 (2002).

Gelmon et al., A phase 1 study of OSI-211 given as an intravenous infusion days 1,2, and 3 every three weeks in patients with solid cancers. Investigational New Drugs, vol. 22:263-275 (2004).

Gelmon et al., Phase 1 Study of the NX211 (liposomal lurtotecan) given as an intravenous infusion on Days 1, 2, & 3 every 3 Weeks in patients (pts) with solid tumors—An NCIC Clinical Trials Group Study. Proceedings of the American Association for Cancer Research, vol. 41:610, Abstract No. 3879 (2000).

Gilbert et al., 9-Nitrocamptothecin liposome aerosol: lack of sub-acute toxicity in dogs. Inhalation Toxicology, vol. 14:185-197 (2002).

Giles et al., Phase I and pharmacokinetic study of a low-clearance, unilamellar liposomal formulation of lurtotecan, a topoisomerase 1 inhibitor, in patients with advanced leukemia. Cancer, vol. 100(7):1449-1458 (2004).

Giles et al., Phase I and pharmacokinetic study of OSI-211, a liposomal formulation of lurtotecan, a topoisomerase I inhibitor, in patients with advanced leukemia. Blood, p. 251 b, Abstract No. 4732 (2003).

Gong et al., Improved lactone stability of 9-nitro-camptothecin in vitro and in vivo by liposomal formulation. Proceedings of the American Association for Cancer Research, vol. 39:430, Abstract No. 2926 (1998).

Gong et al., Sustained organ exposure to 9-nitro-camptothecin (9NC) lactone form by liposomal delivery. Proceedings of the American Association for Cancer Research, vol. 40:417, Abstract No. 2756 (1999).

Gong et al., Development and characterization of liposomal formulation of 9-Nitrocamptothecin. Pharm. Res., vol. 13:S162, Abstract No. PT 6021 (1996).

Green et al., Axonal transport disturbances in vincristine-induced peripheral neuropathy. Ann. Neural., vol. 1 (3):255-262 (1977).

Grit et al., Chemical stability of liposomes: implications for their physical stability. Chemistry and Physics of Lipids, vol. 64:3-18 (1993).

\* cited by examiner

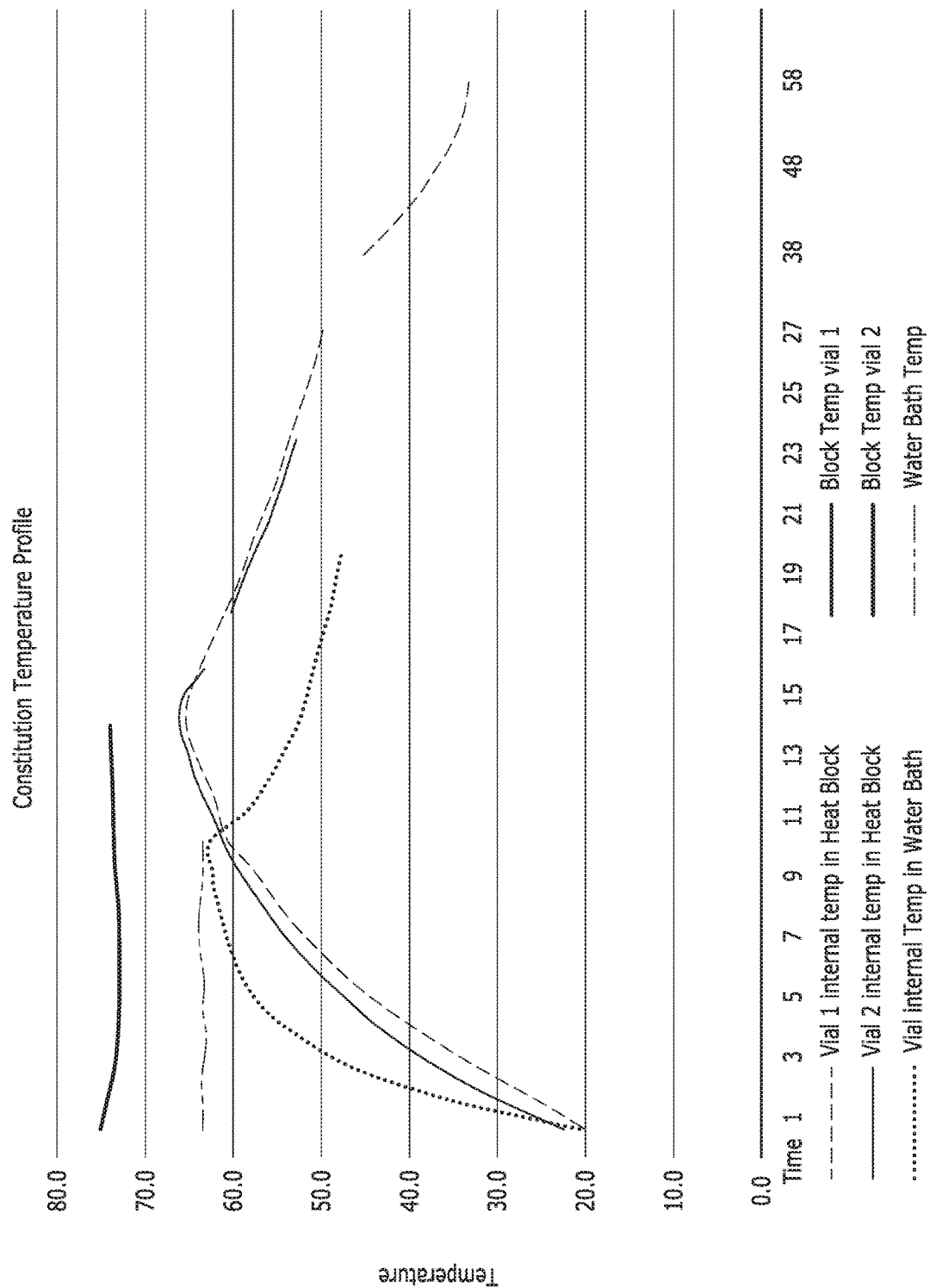

METHOD FOR THE PREPARATION OF LIPOSOME ENCAPSULATED VINCRISTINE FOR THERAPEUTIC USE

RELATED APPLICATIONS

This application claims priority to U.S. Provisional Application No. 61/728,378, entitled "Improved Method for the Preparation of Liposome Encapsulated Vincristine for Therapeutic Use", filed on Nov. 20, 2012, the entirety of which is hereby incorporated by reference.

BACKGROUND

Liposomes are well established nanoparticles that can enhance the efficacy of therapeutically active drugs by improving the plasma distribution and pharmacokinetics of the drugs over non-encapsulated forms (e.g., Weinstein, Liposomes: From Biophysics to Therapeutics, (Ostro, M. J., ed.), Marcel Dekker, Inc., N.Y., pp. 277-338, (1987). For example, Vincristine Sulfate Liposome Injection (VSLI) is a liposome formulation of the anti-cancer therapeutic vincristine sulfate encapsulated in sphingomyelin-cholesterol liposomes which provides greater efficacy than standard vincristine sulfate injection USP (VSI). Clinical trials have also shown that VSLI facilitates dose intensification by significantly extending vincristine's circulation half-life compared to non-encapsulated vincristine. The liposome provides the mechanism for delayed drug release and the liposome size allow the drug to accumulate in cancer tissues by extravasation (Webb et al., Cancer Chemother. Pharmacol 42:461-470, 1998; Shan et al., Cancer Chemother. Pharmacol 58:245-255, 2006). These features translate into improved clinical benefit over the standard VSI.

Encapsulation of vincristine sulfate into sphingomyelin-cholesterol liposomes is typically achieved by using an acidic intraliposomal pH (e.g., pH of 4) and an exterior medium at a neutral pH (e.g., pH of 7). This pH gradient allows the weakly basic vincristine to diffuse into the liposome interior with high efficiency (Cullis et al., Trends in Biotech 9: 268-272, 1991; Boman et al., Bioch Biophys Acta, 1152:253-258, 1993). In order for vincristine to accumulate in the liposome interior with the transmembrane pH gradient, the liposome membrane must become temporarily permeable to the steric bulk of vincristine. Thus, unlike neutral or anionic drugs that often can be passively encapsulated into liposomes, the temperature of the sphingomyelin-cholesterol liposome must be increased in order for the transmembrane pH gradient to function with vincristine. The liposome bilayer, which is an orientation of interlocking sphingomyelin and cholesterol molecules, requires a unique transient heat pattern to create thermotropic disorder transition states. These transition states essentially abate the weak intermolecular bonding between the membrane lipids, creating gaps in interlocking lipids and allow the liposome biolayer to become temporarily permeable. The encapsulation process takes advantage of the spontaneous self reassembly of the sphingomyelin-cholesterol lipids that occurs on cooling back to ambient temperature, which restores the membrane integrity.

This heating profile for drug encapsulation must be balanced with the chemical instability of vincristine to heat exposure (Vendrig et al., Internatl. J. of Pharmaceutics 50:189-196, 1989; Sethi et al., Cancer Res. 45:5386-5389, 1985). Vincristine is thermally labile and readily degrades to N-desformylvincristine in the presence of elevated temperatures. This formamide hydrolysis of vincristine is a well known degradation pathway and affects the stability shelf life of vincristine sulfate injection (VLSI). For example, VLSI solutions cannot be heat sterilized due to this heat lability and must be stored and shipped at refrigerated temperature to realize extended stability.

Accordingly, at the present time Vincristine Sulfate Liposome Injection (VSLI) is prepared from the individual components at a pharmacy according to the directions provided on the FDA-approved label (www.accessdata.fda.gov; Reference ID: 3172211, 2012). These directions include a heating procedure that requires the use of a water bath in order to achieve efficient encapsulation of vincristine in the sphingomyelin-cholesterol liposomes and maintain chemical purity of vincristine. The excellent heat transfer properties of water allow greater than 95% encapsulation of vincristine with no appreciable chemical degradation of the drug.

Since VSLI is an injectable drug, the manufacture of the components and pharmacy preparation are strictly regulated to maintain sterility. Accordingly, the use of an open water bath during preparation of VSLI requires additional resources, planning, and equipment (e.g., floating ring), including an aseptic hood or "clean" room in order to maintain an aseptic environment. In some pharmacies, the constitution of VSLI cannot be done due to the restrictions on maintaining a sterile environment.

Accordingly, there remains a need for improved methods of preparing VSLI that can be efficiently and reproducibly carried out without the additional resources and equipment currently required.

SUMMARY OF THE INVENTION

The current invention is based, at least in part, on the development of a method for preparing VSLI that circumvents the need for the use of a heated water bath during the encapsulation process. Thus, the invention provides efficient, reproducible methods of preparing VSLI which may be widely used with unexpected ease and reduced risk of contamination.

In one aspect, the invention features a method of preparing a pharmaceutically acceptable liquid composition comprising liposome-encapsulated vincristine which is free of substantial degradation products, the method comprising the steps of (a) constituting in a single vial (i) a first solution comprising vincristine sulfate at a concentration of about 1 mg/ml to about 5 mg/ml, wherein the first solution has a pH of about 3.5 to about 5.5; and (ii) a second solution comprising sphingomyelin/cholesterol liposomes at a low pH; (b) raising the pH of the constituting solution in the single vial to a pH of about 7.0 to 7.5; (c) heating the single vial comprising the constituting solution in a dry heat block equilibrated at about 75° C. for at least about 13 to about 18 minutes, wherein said heat block comprises one or more bores about 1-5% larger than the average length or diameter of the single vial to produce a solution comprising constituted liposome encapsulated vincristine; (d) equilibrating the constituted solution to room temperature; (e) diluting a volume of the constituted solution comprising a dose of liposome encapsulated vincristine for the patient of about 1.5 to about 2.4 mg/m$^2$ with a pharmaceutical diluent suitable for intravenous administration, to produce the pharmaceutically acceptable liquid composition; and (f) administering the pharmaceutically acceptable liquid composition to the patient, wherein the constituted solution comprising liposome encapsulated vincristine comprises (i) less than about 2.5% free vincristine; and (ii) less than about 1.5% N-desformylvincristine.

In some embodiments, the first solution comprising vincristine sulfate has pH of about 4.5 to about 4.7. In one embodiment, the first solution further comprises mannitol at a concentration of about 100-200 mg/ml.

In some embodiments, the pH of the second solution comprising the liposomes is about 4.0. In one embodiment, the second solution further comprises a citrate buffer.

In some embodiments, the pH of the constituting solution is raised by the addition of a third solution comprising a buffer at a pH of about 9.0. In one embodiment, the third solution comprises sodium phosphate buffer.

In some embodiments, the constituting solution comprises a concentration ratio of about 0.1/1.0 to about 0.2/2.0 vincristine sulfate to lipid.

In some embodiments, the concentration of vincristine sulfate in the constituted solution is about 0.1 mg/mL to about 0.5 mg/mL. In some embodiments, the concentration of vincristine sulfate in the constituted solution is about at about 0.15 mg/mL to about 0.2 mg/mL. In one embodiment, the concentration of vincristine sulfate in the constituted solution is about 0.16 mg/mL.

In one embodiment, the first solution comprises vincristine sulfate USP (5 mg/5 mL), which is equivalent to 4.5 mg/5 mL vincristine free base, and 500 mg/5 mL mannitol, the second solution comprises sphingomyelin/cholesterol liposomes consisting of 73.5 mg/mL sphingomyelin, 29.5 mg/mL cholesterol, 33.6 mg/mL citric acid, 35.4 mg/mL sodium citrate, and the third solution comprises 355 mg/25 mL dibasic sodium phosphate and 225 mg/25 mL sodium chloride.

In some embodiments, the ratio of sphingomyelin to cholesterol in the liposome is between about 75/25 mol %/mol sphingomyelin/cholesterol to 30/50 mol %/mol % sphingomyelin/cholesterol. In some embodiments, the liposomes comprise about 70/30 mol %/mol sphingomyelin/cholesterol to 40/45 mol %/mol % sphingomyelin/cholesterol. In one embodiment, the liposomes comprise approximately 55/45 mol %/mol % sphingomyelin/cholesterol. In another embodiment, the liposomes comprising about 60/40 mol %/mol % sphingomyelin/cholesterol.

In some embodiments, the liposomes have a size range of about 0.05-0.5 microns. In some embodiments, the liposomes have a mean diameter of about 50-200 nm. In one embodiment, the liposomes have a mean diameter of about 90-125 nm.

In some embodiments, the constituting solution has a volume of between about 20-50 mL. In some embodiments, the constituting solution has a volume of between 30-35 mL.

In some embodiments, the heat block is equilibrated to 75±2° C. for about 15 minutes prior to insertion of the vial containing the constituting solution. In some embodiments, the constituting solution is heated for about 13-15 minutes within the caliber bore of a dri-block equilibrated at 75±2° C. In one embodiment, the constituting solution is heated for 14 minutes±30 seconds within the caliber bore of a dri-block equilibrated at 75±2° C.

In some embodiments, the bores in the heat block are less than about 3% larger than the average length or diameter of the single vial containing the constituting solution. In some embodiments, the single vial containing the constituting solution has a diameter between about 35.8 to about 37.3 mm, and the caliber bores in the heat block are cylindrical with a diameter between 37.2 to 37.8 mm in diameter.

In some embodiments, the constituted solution is equilibrated to room temperature for at least about 30 minutes.

In some embodiments, the volume of the constituted solution comprising a dose of liposome encapsulated vincristine for the patient of about 1.5 to about 2.4 mg/m$^2$ is diluted with standard pharmaceutical diluents suitable for intravenous administration, to produce the pharmaceutically acceptable liquid composition. In some embodiments, the volume of the patients calculated dose is removed from an infusion container and replaced with the calculated volume of the constituted VSLI solution.

In some embodiments, the pharmaceutically acceptable liquid composition comprising liposome-encapsulated vincristine is administered to the patient within no more than 24 hours after constitution.

The VSLI produced according to the methods of the invention are typically administered to a patient having cancer. In some embodiments, the cancer is lymphoma, leukemia, myeloma, brain cancer or neuroblastoma.

In some embodiments, the pharmaceutically acceptable liquid composition comprising liposome-encapsulated vincristine is administered by intravenous infusion over a period of about 30 to 60 minutes. In some embodiments, the pharmaceutically acceptable liquid composition comprising liposome-encapsulated vincristine is administered by intravenous infusion once every 7-28 days. In one embodiment, the pharmaceutically acceptable liquid composition comprising liposome-encapsulated vincristine is administered by intravenous infusion once every 7 days.

BRIEF DESCRIPTION OF THE DRAWINGS

FIG. 1 is a graph depicting the internal heating profile of a constituted solution containing vincristine sulfate and sphingomyelin/cholesterol liposomes using a dry block and water bath.

DETAILED DESCRIPTION

The present invention overcomes the deficiencies associated with the use of a water bath during the currently used methods of preparing VLSI. Surprisingly, it was discovered that the use of a heating block with a custom designed insert designed to conform to the container used for constituting the VSLI provides the heat profile needed to achieve uniform encapsulation of vincristine without significant degradation.

In addition, the improved ability of the methods of preparing VSLI described herein to demonstrate parametric release is significant. Since the stability of VSLI warrants "just in time" preparation, the constitution process must be highly efficient and reproducible by the pharmacist. The pharmacist needs to know (i.e., parametrically) that the encapsulation has been achieved by the heat induced process because it provides "a system of release that gives the assurance that a product is of the intended quality based on the review of information collected during the constitution process and on the compliance with specific GMP requirements related to parametric release" (Annex 17 EU guidance).

The heating block procedure of the present invention provides a convenient and compliant process to achieve constitution of VSLI with greater than 95% encapsulation efficiency. Since it involves fewer steps, the probability of operational errors is decreased. The process is overall more straightforward, takes less time, uses fewer resources, and is convenient for routine pharmacy operation. Additionally, the individual preparing the VSLI need not deal with potential microbial contamination from microbes growing in the water bath or water vapor from the heated water bath.

Defintions

Unless specifically noted otherwise, all technical and scientific terms used herein have the standard definitions commonly understood by one of ordinary skill in the art of therapeutic and pharmaceutical science.

The singular form "a," "an," and "the" include plural reference unless the context clearly dictates otherwise.

The terms "comprise" and comprising" are used in the inclusive, open sense, meaning that additional elements may be included.

The term "about", particularly in reference to a given quantity or number, is meant to encompass deviations of plus or minus five percent.

A "sterile" composition or container, as used herein, is free of viable microbes as determined using the USP sterility test. (See, "The United States Pharmacopeial Convention: 2008).

"Liposome" "vesicle" and "liposome vesicle" will be understood to indicate structures having lipid-containing membranes enclosing an aqueous interior. The structures may have one or more lipid membranes unless otherwise indicated, although generally the liposomes will have only one membrane. Such single-layered liposomes are referred to herein as "unilamellar". Multilayer liposomes are referred to herein as "multilamellar".

A "standard" therapeutic agent, or "free" therapeutic agent, refers to a therapeutic agent that is not liposome-encapsulated. Usually, a drug is presumed to be "standard or "free" unless specified otherwise. A standard *vinca* alkaloid in free form may still be present in combination with other reagents, however, such as other chemotherapeutic compounds, a pharmaceutical carrier, or complexing agents, i.e. as used herein the term only specifically excludes lipid formulations of the *vinca* alkaloids.

The phrase "just in time" refers to the combining the separate components of a drug product (e.g., VSLI) shortly (e.g., within 24 hours or less) before administration to the patient in order to maintain the quality of the drug product (e.g., minimize degradation).

"Systemic delivery," as used herein, refers to delivery that leads to a broad bio-distribution of a compound within an organism. Systemic delivery means that a useful, preferably therapeutic, amount of a compound is exposed to most parts of the body. To obtain broad bio-distribution generally requires a route of introduction such that the compound is not rapidly degraded or cleared (such as by first pass organs (liver, lung, etc.) or by rapid, nonspecific cell binding) before reaching a disease site. Systemic delivery of liposome-encapsulated *vinca* alkaloids is preferably obtained by intravenous delivery.

The phrase "therapeutically effective amount" refers to an amount of drug (e.g., VSLI) effective to treat a disease or disorder (e.g., cancer) in a mammal, for example, resulting in stable disease, partial remission or complete remission of the cancerous state.

A "stable disease," as used herein, refers to a state wherein administration of the drug (e.g., VSLI) causes cessation of the growth or prevalence of a tumor or cancer as measured by standard clinical, radiological and/or biochemical means, although there is no regression or decrease in the size or prevalence of the cancer.

A "Partial response" or "partial remission" refers to the amelioration of a cancerous state, as measured by standard clinical, radiological and/or biochemical means, in response to treatment. Typically, a "partial response" means that the size of a tumor or the level of a cancer-indicating blood marker has decreased from a baseline level (e.g., 20%, 30%, 40% or 50%) in response to treatment. For example, for treatment of blood cancers the responses are assessed based on the international working group criteria (International Working Group (IWS) criteria; B D Cheson et al, J Clin Oncol 15:4642-4649).

A "complete response" or "complete remission" means that a cancerous state, as measured by, for example, tumor size and/or cancer marker levels, is undetectable following treatment.

"Neurological toxicity" includes symptoms of neuropathy, such as hypoesthesia, hyperesthesia, paresthesia, hyporeflexia, areflexia, neuralgia, jaw pain, decreased vibratory sense, cranial neuropathy, ileus, burning sensation, arthralgia, myalgia, muscle spasm, weakness, and/or orthostatic hyptension both before and during treatment. Orthostatic hypotension may occur. A Neurological toxicity is assessed as being Grade 1 to Grade 3 based on the National Cancer Institute (NCI) Common Terminology Criteria for Adverse Events (CTCAE) version 4.03 (http://ctep.cancer-.gov/reporting/etc.html).

Vincristine Sulfate

Vincristine sulfate is a member of a *vinca* alkaloid family originally isolated from the periwinkle plant (*Catharanthus roseus*). Vincristine Sulfate has cell-cycle specific anticancer activity. The *vinca* alkaloid bind to tubulin, altering tubulin polymerization leading to metaphase arrest, inhibition of cell mitosis, and cell death. As a cell cycle specific agent its' therapeutic response is advanced by liposome encapsulation which maintains extended drug levels. Prolonged exposure of cells to vincristine (and other cell cycle specific drugs) has been shown to enhance in-vitro cytotoxicity of the drug (Bfurris et al, JNCI 84; 1816-1826, 1992; Georgiadis et al., Clin Cancer Res 3:449-454, 1997; Jackson and Bender, Cancer Res 39:4346-4349, 1979).

Vincristine sulfate is commonly isolated as a 1:1 sulfate salt. It is a hygroscopic, white to slightly yellowish crystalline powder that is soluble in water. It has a molecular weight of 923.04 (salt form)/824.98 (base form) and a molecular formula of $C_{46}H_{56}N_4O_{10} \cdot H_2SO_4$. The chemical name for vincristine sulfate is 22-oxovincaleukoblastine and it has the following chemical structure:

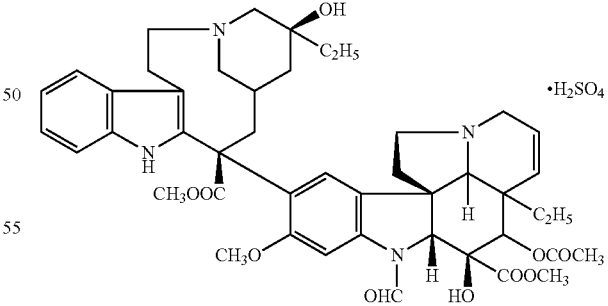

Vincristine sulfate is prescribed as vincristine sulfate injection USP (e.g., as a 1 mg/mL solution) and is also known as leurocristine sulfate, Kyocristine, vincosid, vincrex, oncovin, Vincasar PFS®, is commercially available from any of a number of sources.

Liposomes

The liposome carrier component of the present invention are comprised of sphingomyelin and cholesterol liposomes injection (SCLI). The ratio of sphingomyelin to cholesterol present in the liposome may vary, but generally is in the range of from 75/25 mol %/mol sphingomyelin/cholesterol to 30/50 mol % mol % sphingomyelin/cholesterol. In one embodiment, the liposome composition comprise about 70/30 mol % mol sphingomyelin/cholesterol to 40/45 mol % mol % sphingomyelin/cholesterol. In another embodiment, the liposome compositions comprise approximately 55/45 mol % mol % sphingomyelin/cholesterol. In still another embodiment the liposome compositions comprise about 60/40 mol % mol % sphingomyelin/cholesterol.

In certain embodiments, additional lipids may be present in the formulations, for example, to prevent lipid oxidation or to attach ligands onto the liposome surface. Generally, the inclusion of other lipids will result in a decrease in the sphingomyelin/cholesterol ratio.

The sphingomyelin/cholesterol liposomes used in the present invention can be multilamellar or unilamellar. Suitable methods for preparing the liposomes include, but are not limited to, sonication, extrusion, high pressure/homogenization, microfluidization, detergent dialysis, calcium-induced fusion of small liposome vesicles, thin film evaporization, and ether-infusion methods, all of which are well known in the art. For example, a variety of methods are available for preparing liposomes as described in, e.g., Szoka, et al., Ann. Rev. Biophys. Bioeng., 9:467 (1980), U.S. Pat. Nos. 4,186,183, 4,217,344, 4,235,871, 4,261,975, 4,485,054, 4,501,728, 4,774,085, 4,837,028, 4,946,787, 5,543,152, 6,723,338, WO 91/17424, Deamer and Bangham, Biochim. Biophys. Acta, 443:629 634 (1976); Fraley, et al., Proc. Natl. Acad. Sci. USA, 76:3348 3352 (1979); Hope, et al., Biochim. Biophys. Acta, 812:55 65 (1985); Mayer, et al., Biochim. Biophys. Acta, 858:161 168 (1986); Williams, et al., Proc. Natl. Acad. Sci., 85:242 246 (1988), the text Liposomes, Marc J. Ostro, ed., Marcel Dekker, Inc., New York, 1983, Chapter 1, and Hope, et al., Chem. Phys. Lip., 40:89 (1986), all of which are incorporated herein by reference.

Following liposome preparation, the liposomes can be sized to achieve the desired particle size range using standard methods well-known in the art (e.g., see U.S. Pat. No. 6,723,338). Typically liposomes which can be used in the VSLI preparations described herein have a size range of about 0.05-0.5 microns (50-500 nm), 0.2-0.4 microns (200-400 nm), about 0.1-0.4 microns (100-400 nm), about 0.05-0.2 (50-200 nm) or about 0.5 (500 nm) to about 0.15 microns (150 nm). In certain embodiments, the liposomes have a particle size having a mean particle diameter of about 50 nm, about 60 nm, about 70 nm, about 80 nm, about 90 nm, about 100 nm, about 105 nm, about 110 nm, about 115 nm, about 120 nm, about 130 nm, about 140 nm, about 150 nm, about 160 nm, 170 nm, about 180 nm, about 190 nm, or about 200 nm. In one embodiment, the average particle size is between 90 and 125 nm with the preferred average particle size about 107.5 nm, where 25% of the particle size distribution is not less than 70 nm and where 90% of the distribution has a particle size of not more than 170 nm.

The sphingomyelin/cholesterol liposomes function as the liposome component used in the VSLI preparations described herein and are manufactured so that the liposome interior has a low pH. During the constitution process VSI, having a low pH, and SPLI, having a low pH, are diluted in a buffer of a higher pH whereby the final pH of the external VSLI solution is about physiologically neutral. The result is the creation of a pH gradient across the lipid membrane in which the pH is lower in the interior core of the liposomes than the exterior surrounding solution. Such gradients are achieved according to known methods (e.g., U.S. Pat. No. 6,723,338). For example, gradients can be achieved by formulating the liposomes in the presence of a buffer with a pH between about 2 and about 6, a pH between about 3 and about 5, and then subsequently transferring the liposomes to a higher pH, for example, of about 7.0 to about 7.5. In one embodiment, the liposomes have an interior pH of about 4.0. Any number of dilution buffers can be used, such as sodium phosphate. In one embodiment the buffer has a pH of 8-10, preferably 9.0, so that the final diluted external liposome solution when mixed with VSI and SPLI will have a physiologic neutral pH.

Prior to use in the preparation of VSLI according to the methods described herein, the SPLI liposomes can be stored at refrigerated conditions for substantial periods of time prior to drug encapsulation and constitution of VSLI for administration to a patient. Alternatively, the liposomes can be dehydrated, stored and then rehydrated prior to use in accordance with well-known methods (See, e.g., U.S. Pat. Nos. 5,077,056 or 5,736,155).

VSLI Preparation

VSLI is prepared with strict aseptic techniques, for example, in a biological safety cabinet or by established pharmacy safety procedures for the preparation of sterile injectable formulations and hazardous drugs. Procedures for handling and disposal of anticancer drugs must be strictly followed (NIOSH Alert: Preventing occupational exposure to antineoplastic and other hazardous drugs in healthcare settings. 2004. U.S. Department of Health and Human Services, Public Health Service, Centers for Disease Control and Prevention, National Institute for Occupational Safety and Health, DHHS (NIOSH) Publication No. 2004-16; OSHA Technical Manual, TED 1-0.15A, Section VI: Chapter 2. Controlling Occupational Exposure to Hazardous Drugs. OSHA, 1999; American Society of Health-System Pharmacists. ASHP guidelines on handling hazardous drugs. Am J Health-Syst Pharm. (2006) 63:1172-1193; Polovich M, White J M, Kelleher L O (eds.) 2005. Chemotherapy and biotherapy guidelines and recommendations for practice (2nd. ed.) Pittsburgh, Pa.: Oncology Nursing Society)

The process for preparing constituted VSLI includes the following general steps:

A constituting solution is prepared by mixing in a sterile container a first solution of vincristine sulfate containing between about 1 mg/mL, about 2 mg/mL or about 5 mg/mL in a buffer containing about 100 to about 200 mg/mL mannitol (other pharmaceutically acceptable excipients in which vincristine sulfate remains stable can also be used) at a pH of about 3.5 to about 5.5, or about 4.5 to about 4.7, with a second solution of liposomes suspended in a buffer at low pH (e.g., about 4.0) at an appropriate concentration ratio, for example, 0.1/1.0 to 0.2/1.0 (weight vincristine sulfate to weight lipid).

The pH of the constituting solution containing the vincristine sulfate and liposomes is then raised to about 7.0 to about 7.5 to create a pH gradient. This can be accomplished, for example, by the addition of a buffer (e.g., sodium phosphate) at a higher pH (e.g., about 9.0).

The constituting solution is then heated for at least about 13 to about 18 minutes in a dry heat block equilibrated to about 75° C., which contains caliber wells less than about 5%, larger than the average length or diameter of the container containing the constituting solution to produce the constituted product, VSLI.

The heated, constituting solution comprising the constituted product is then allowed to equilibrate for at least about 30 minutes, at least about 45 minutes or at least about 60 minutes to room temperature (15° C. to 30° C.,).

A volume of the constituting solution corresponding to the dose of the constituted VSLI to be administered to the patient is then admixed with a solution suitable for intravenous administration to a final volume of about 100 mL.

In some embodiments, solutions of vincristine sulfate, liposomes and high pH buffer are provided in three separate containers. In certain embodiments, the three solutions are constituted into one sterile container with a capacity to contain the combined volume of the solutions, for example, about 20-50 mL, about 25-40 mL, or about 30-35 mL.

In one embodiment, the separate components are provided as a kit including 3 or more vials. At least one of the vials contains a vincristine solution containing, e.g., 1 mg/mL, 2 mg/mL, or 5 mg/mL vincristine sulfate in buffer containing, e.g., 100 or 200 mg/mL mannitol (other excipients that are pharmaceutically acceptable, and in which vincristine remains stable for extended periods, can also be used), and adjusted to pH 3.5 to 5.5, or preferably pH 4.5 to pH 4.7. One of the vials contains a solution comprising sphingomyelin and cholesterol liposomes suspended in a 300 mM citrate buffer at, e.g., pH 4.0. Another vial or vials contains an alkaline phosphate buffer (e.g., pH 9.0) such as dibasic sodium phosphate, 14.2 mg/ml (20 ml/vial).

In one embodiment, the ingredients for the constitution of VSLI are provided separately in three vials containing (i) vincristine sulfate USP (5 mg/5 mL), which is equivalent to 4.5 mg/5 mL vincristine free base, and 500 mg/5 mL mannitol; (ii) sphingomyelin/cholesterol liposomes injection (SPLI) consisting of 73.5 mg/mL sphingomyelin, 29.5 mg/mL cholesterol, 33.6 mg/mL citric acid, 35.4 mg/mL sodium citrate, and not more than 0.1% ethanol; and (iii) Sodium phosphate injection (SPI) containing 355 mg/25 mL dibasic sodium phosphate and 225 mg/25 mL sodium chloride all prepared with water for injection.

The containers used in the methods of the invention are sterile and composed of any pharmaceutically acceptable substance (e.g., glass or plastic). There are a number of different vial types and sized that are commercially marketed by a number of different manufacturers (e.g., Wheaton Products, Thomas Scientific). In one embodiment, the components are constituted in a sterile vial with an average diameter of about 36.5 mm, and an average range of about 35.8 to about 37.3 mm.

Suitable dry block heaters, which provide a safe, dry, constant temperature source, are commercially available from a number of sources (e.g, Bibby Scientific Ltd, V&P Scientific, Inc., Fisher Scientific Inc., VWR Scientific, Thermolyne Inc.). Heat conductive inserts having one or more calibrated bores adapted to receive the container of constituting solution may be metal (e.g., anodized aluminum, copper) or other suitable heat conductive materials. Inserts containing bores of openings of the appropriate size can be readily obtained (e.g., V&P Scientific, Inc.), or manufactured using standard methods. In certain embodiments, the heat block contains openings that are between about 1-5%, or about 4.5%, 4.2%, 4.0%, 3.8%, 3.5%, 3.3%, 3.0%, 2.8%, 2.5%, 2.2%, 2.0%, 1.8%, 1.5%, 1.2% or 1.0% larger than the average length or diameter of the container containing the constituting solution. In some embodiments, the heat block contains cylindrical openings. In one embodiment, the openings are between 37.2 to 37.8 mm in diameter, or between about 37.4 to 37.6 mm in diameter.

In some embodiments, the constituting solution is heated for about 13 minutes, about 14 minutes, about 15 minutes, about 16 minutes, about 17 minutes at about 75° C. In one embodiment, the constituting solution is heated for about 14 minutes in at heat block equilibrated at 75° C.

The constituted VSLI may be admixed with a pharmaceutically acceptable diluent suitable for intravenous administration to the patient (e.g., dextrose, sodium chloride) which may be provided, for example in a pre-filled, sterile container (glass bottle, plastic bottle or plastic bag). In some embodiments, the volume of the patients calculated dose is removed from an infusion bag and replaced with the calculated volume of the constituted VSLI solution into an infusion bag, for example, where the final volume of the infusion container will be 100 mL. In one embodiment, the pharmaceutically acceptable diluents is of 5% Dextrose Injection or 0.9% Sodium Chloride Injection.

VSLI

The VSLI produced according to the methods described herein appears as a white to off-white, translucent suspension, essentially free of visible foreign matter and aggregates. Typically, greater than about 95%, about 96%, about 97%, about 98% or more of the vincristine sulfate is encapsulated in the liposomes.

The VSLI produced according to the methods described herein contains total impurities of less than about 4.0%, 3.5%, 3.4%, 3.2%, 3.1% or 3.0%. In some embodiments, the VSLI contains less than about 2.0%, 1.8%, 1.7%, 1.6%, 1.5%, 1.4% or 1.3% N-desformylvincristine.

The VSLI produced according to the methods described herein has an average in vitro release rate (IVR) or in vivo release rate of at least about 75%, 76%, 77%, 78%, 79%, 80%, 81%, 82%, 83%, 84% or about 85% within 72 hours.

Assays for determining the level of vincristine encapsulation, the levels of impurities and release rates of vincristine from liposomes are known in the art. See, for example, U.S. Pat. Nos. 5,543,152 and 5,837,282; Zhigalstev et al. J. Controlled Release 104:103-111, 2005); Puscalau et al. Am. J. Health-Syst. Pharm. 62:1606-1612, 2005).

Generally, the VSLI produced according to the methods described herein contains vincristine sulfate at about 0.1 mg/mL to about 0.5 mg/mL. In certain embodiments, the vincristine sulfate is present at about 0.15 mg/mL to about 0.2 mg/mL. In one embodiment, the vincristine sulfate is present at about 0.16 mg/mL. In one embodiment, the VSLI contains 5 mg vincristine sulfate, 500 mg mannitol, 73.5 mg sphingomyelin, 29.5 mg cholesterol, 36 mg sodium citrate, 38 mg citric acid, 355 mg sodium phosphate, and 225 mg sodium chloride.

Dosage and Administration

VSLI prepared according to the methods described herein can be used to treat any type of cancer including primary, relapsed and refractory cancers. The patient or subject treated with the VLSI may be a variety of animals, including humans, non-human primates, avian species, equine species, canine species, feline species, bovine species, swine, lagomorphs, rodents, and the like. In certain embodiments, the VSLI is used to treat cancers of the blood and lymphatic systems including, but not limited to, lymphomas, leukemias and myelomas. In certain embodiments, the VSLI is used to treat tumors including, but not limited to neuroblastomas and brain cancers.

The VSLI can be used as a single agent or in combination with other chemotherapeutic agents, such as cyclophosphamide, doxorubicin and/or prednisone. In one embodiment, the VSLI is administered along with as cyclophosphamide, doxorubicin and prednisone as a liposomal CHOP formulation ("lipo-CHOP). In another embodiment, the VSLI is co-administered with at least one additional anti-tumor agent. In another embodiment, the additional anti-tumor agent is an anti-tumor monoclonal antibody, such as Oncoly™, Rituxan™, or Bexxar™. In another embodiment, the additional anti-tumor agent is an antisense drugs or an anti-tumor vaccine. In another embodiment, the VSLI is co-administered with a prophylactic or therapeutic treatment for neurotoxicity, such as gabapentin (Neurontin™).

Typically, the VSLI is prepared within about 24 hours of administration to the patient and is stored at room temperature (15° C. to 30° C.,) or refrigerated (2-8° C.).

The VSLI is administered to the patient systemically by intravenous delivery. In one embodiment, the VSLI is administered by intravenous infusion over a period of, e.g., about 30 minutes, about 45 minutes, about 60 minutes, about 90 minutes or longer.

Typically, the VSLI is administered periodically, e.g., once every 7-28 days. In certain embodiments, the VSLI is administered once every 3, 5, 7, 10, 14, 21 or 28 days. In one embodiment, the VSLI is administered by intravenous infusion every 14 days. In another embodiment, the VSLI is administered by intravenous infusion every 7 days. As used herein, each administration of VSLI is considered one "course" of treatment.

The amount of VSLI administered per dose will depend on a number of factors, such as the medical history of the patient, the use of other therapies, and the nature of the disease (e.g., first line, relapsed or refractory cancer). Typically, the VSLI prepared according to the methods described herein is administered at a dosage of about 1.4 to about 2.4 mg/m$^2$. In certain embodiments, the VSLI is administered at a dose of about 1.5 mg/m$^2$, about 1.8 mg/m$^2$, about 2.0 mg/m$^2$, 2.1 mg/m$^2$, 2.2 mg/m$^2$, 2.3 mg/m$^2$ or 2.4 mg/m$^2$ (i.e., mg vincristine per m$^2$ body surface area). In one embodiment, the VSLI is administered at a dose of 2.25 mg/m$^2$ by intravenous infusion over about 60 minutes once every 7 days.

In other embodiments, the dose of VSLI may be temporarily interrupted and/or reduced during treatment. For example, in one embodiment, the dosage of VSLI administered to a patient portraying a Grade 3 peripheral neuropathy or persistent Grade 2 peripheral neuropathy may be discontinued for up to about 7 days, and then reduced to a dose of about 2 mg/m$^2$ upon recovery to Grade 1 or 2. In another embodiment, the dosage administered to a patient portraying a persistent Grade 2 peripheral neuropathy, even after receiving a reduced dose, may be discontinue for up to 7 days, and then reduced to dose of 1.825 mg/m$^2$, or a dose of 1.5 mg/m$^2$.

The dosage of VSLI is determined by calculating the body surface area (BSA) of the subject according to well-known methods. For example, according to Mosteller's formula in which the BSA equals the square root of product of the weight of the subject in kg times the height in cm divided by 3600. The "normal" BSA in humans is generally taken to be 1.7 m$^2$ but also depends on other factors including the age and gender of the individual. For example:

Average BSA for adult men: 1.9 m$^2$
Average BSA for adult women: 1.6 m$^2$
Average BSA for children (9 years): 1.07 m$^2$
Average BSA for children (10 years): 1.14 m$^2$
Average BSA for children (12-13 years): 1.33 m$^2$
(Mosteller RD. Simplified calculation of body-surface area. N Engl J Med 1987; 317:1098)

EXAMPLES

Example 1

The temperature profile of the VSLI vial solution was investigated during the heating with the dry block process and compared with that of the temperature profile observed when heating with a water bath following the approved label instructions for Marqibo® (FDA/cder Reference ID: 3172211, August 2012).

Equipment and Materials

Marqibo® kit constituted VSLI, lot NT 268035 (contents of partially used vials combined into one vial
Techne Dri-Block® DB-3 heater equipped with 1.480" diameter well and thermometer pocket (Bibby Scientific Limited).
Digital thermometers; accurate to ±1° C. in the range of 0°-100° C.
Isotemp 202 #00947 water bath (Fisher Scientific)
Fluke 726 #914002 thermo-couple temperature calibrator (Fluke Corporation)

Procedure

Temperature profile measurements were generated by recording the solution temperature inside the vial after being placed in the heating apparatus (i.e., dry block or water bath). Time zero was the point where the vial was placed in the heating apparatus. The following procedure was used:

1. The components, VSI and SCLI, were combined into a single SPI vial (Swiss Precision Instruments, Inc.). A digital thermocouple was inserted through the septum of the vial and held approximately 5 mm from the bottom surface of the vial and positioned in the middle of the liquid solution.
2. The dry block heater was used with a block containing a 1.480 inch vial container hole. The block temperature was monitored by placing a thermometer into the block's thermometer hole, which is situated in proximity to the vial container hole. The block heater was set to a temperature of 75° C. and allowed to warm until the block thermometer read 75±2° C. The heated block was equilibrated for a minimum of 15 minutes at 75±2° C. The vial was then inserted into the well of the 75±2° C. equilibrated block for 14 minutes±15 seconds, and then removed. The constituted vial was allowed to come to ambient temperature by placing in ambient conditions for about 60 minutes. The procedure was repeated twice using the same vial.
3. Vial internal liquid temperature, and block temperatures were recorded at 1 minute intervals (or as noted) and tabulated in Table 1.
4. For comparison, the water bath was allowed to heat until the water temperature was 65±5° C. The water bath was equilibrated for a minimum of 15 minutes. The vial containing constituted VSLI was then inserted into the water bath for 10 minutes±1 minute, and then removed. The constituted vials were allowed to come to ambient temperature.
5. Vial internal liquid temperature, time and water temperature were recorded and tabulated in Table 1.

Results and Discussion

The temperature profile of heating the liquid contents of a constituted VSLI vial with a dry block equilibrated at 75°±2° C., demonstrate an even and gradual heating rate to 65°±5° C. The results tabulated in Table 1 and FIG. 1 show that the dry block heated the liquid vial contents at a mean rate of 3.26° C./minute as compared to the water bath, which heated the vial contents at a mean rate of 4.21° C./minute. The desired temperature of 65°±5° C. was achieved in 14 minutes in the dry block compared to the water bath which took 10 minutes. With both heating apparatuses, once the vial was removed from the heating source there was gradual cooling. The temperature remained within 59-65° C. for 3-4 minutes following removal from the dry block and 1-2 minutes following removal from the water bath. With both apparatuses, the vial was exposed to 50-65° C. for at least 20 minutes with the dry block and 15 minutes with the water bath. Following heating in either apparatus, the solutions remained visually identical: a white to off-white, translucent suspension essentially free of visible foreign matter and aggregates.

TABLE 1

Constitution Temperature Profile*

| Time | Internal Temp HB | Block Temp | Internal temp HB | Block temp2 | Internal temp WB | Water Bath |
|---|---|---|---|---|---|---|
| 0 | 20.3 | 75.3 | 22.8 | 75.4 | 20.9 | 63.8 |
| 1 | 25.6 | 74.7 | 29.9 | 74.8 | 35.4 | 63.8 |
| 2 | 31.6 | 74.0 | 36.1 | 74.0 | 45.6 | 63.9 |
| 3 | 37.0 | 73.5 | 41.3 | 73.6 | 51.7 | 63.4 |
| 4 | 41.9 | 73.3 | 45.5 | 73.4 | 56.1 | 63.7 |
| 5 | 46.2 | 73.2 | 49.1 | 73.4 | 58.8 | 63.6 |
| 6 | 49.8 | 73.2 | 52.4 | 73.4 | 60.3 | 64.0 |
| 7 | 53.0 | 73.3 | 55.2 | 73.4 | 61.3 | 64.4 |
| 8 | 55.6 | 73.4 | 57.5 | 73.5 | 62.2 | 64.0 |
| 9 | 57.9 | 73.6 | 59.7 | 73.8 | 62.7 | 63.8 |
| 10 | 60.8 | 73.8 | 61.4 | 73.9 | 63.0 | 63.8 |
| 11 | 62.1 | 73.9 | 62.8 | 74.1 | 59.0 | NR |
| 12 | 63.3 | 74.1 | 64.4 | 74.2 | 56.6 | NR |
| 13 | 64.6 | 74.1 | 65.4 | 74.3 | 54.8 | NR |
| 14 | 65.8 | 74.3 | 66.4 | 74.4 | 53.1 | NR |
| 15 | 65.6 | NR | 66.1 | NR | 52.0 | NR |
| 16 | 64.1 | NR | 63.7 | NR | 51.2 | NR |
| 17 | 62.7 | NR | NR | NR | 50.3 | NR |
| 18 | 61.2 | NR | 60.6 | NR | 49.3 | NR |
| 19 | 59.8 | NR | 59.3 | NR | 48.7 | NR |
| 20 | 58.6 | NR | 58.0 | NR | 48.0 | NR |
| 21 | 57.4 | NR | 56.5 | NR | NR | NR |
| 22 | 56.1 | NR | 55.3 | NR | NR | NR |
| 23 | 55.0 | NR | 54.2 | NR | NR | NR |
| 24 | 53.9 | NR | 53.2 | NR | NR | NR |
| 25 | 52.8 | NR | NR | NR | 44.4 | NR |
| 26 | 51.7 | NR | NR | NR | NR | NR |
| 27 | 50.8 | NR | NR | NR | NR | NR |
| 28 | 49.8 | NR | NR | NR | NR | NR |
|  | NR | NR | NR | NR | NR | NR |
| 33 | 45.6 | NR | NR | NR | NR | NR |
| 38 | 42.3 | NR | NR | NR | NR | NR |
| 43 | 39.4 | NR | NR | NR | NR | NR |
| 48 | 37.3 | NR | NR | NR | NR | NR |
| 53 | 35.3 | NR | NR | NR | NR | NR |
| 58 | 33.9 | NR | NR | NR | NR | NR |
| 60 | 33.3 | NR | NR | NR | NR | NR |

*Internal Temp HB = internal temperature of vial contents heated in the dry block
Internal Temp WB = internal temperature of the vial contents heated in the water bath
NR = Not recorded Conclusion This study demonstrated that the dry block proved a suitable temperature heating profile that allows the VSLI vials internal liquid temperature to achieve 65°±5° C. within 14 minutes, and provided a heating exposure in the 50-65° C. range of 20 minutes. This compares to the heating the vials in a water bath, which achieves an internal liquid temperature of 65°±5° C. in 10 minutes, and an overall heating exposure in the 50-65° C. range of 15 minutes. The rate of heating for both methods was gradual and even. The dry block set at 75°±2° C. produced a heating rate of 3.26° C. per minute, and the water bath set at 65°±5° C. produced a rate of 4.21° C. per minute. The heating leveled off with the water bath, while the rate of the heating in the dry block continued at a steady rate toward the 75°±2° C. set point. Cooling to ambient temperature took about 60 minutes once the vials were removed from either heating apparatus. These heating profiles suggest that the near quantitative encapsulation of vincristine is a thermodynamic process which is dependent on the overall exposure to temperatures that promote membrane encapsulation rather than the kinetics of achieving those conditions.

In summary, the dry block and water bath can provide a thermodynamic profile that allows encapsulation of vincristine into the sphingomyelin cholesterol liposomes for the efficient preparation of VSLI.

Example 2

The levels of vincristine degradant products of VSLI constituted using a dry heat block were investigated.

Equipment and Materials:
  Techne DB-3 Dri-Block® equipped with 1.480" diameter well and thermometer pocket.
  Thermometer with a diameter no greater than 7 mm, and accurate to ±1° C. in the range of 0°-100° C.
  Calibrated stopwatch or timer
  Micrometer (0-2") or equivalent.
  30 Marqibo® Kits, Lot # TTX0611 (Talon Therapeutics, Inc.)

Procedure

Vials from 30 Marqibo® kits having SPI vials with the maximum and minimum outer diameters were used in the study. The diameter of the SPI vials was measured and recorded to the nearest 0.001". Results are shown in Table 2.

TABLE 2

Vial Identification and SPI Vial Diameter

| Vial Identification | SPI Vial Diameter (±0.0001 in.) | Study Allocation |
|---|---|---|
| 1 | 1.4350 |  |
| 2 | 1.4360 |  |
| 3 | 1.4340 |  |
| 4 | 1.4350 |  |
| 5 | 1.4490 |  |
| 6 | 1.4455 |  |
| 7 | 1.4330 |  |
| 8 | 1.4370 |  |
| 9 | 1.4350 |  |
| 10 | 1.4315 |  |
| 11 | 1.4405 |  |
| 12 | 1.4545 | kit 2 |
| 13 | 1.4335 |  |
| 14 | 1.4370 |  |
| 15 | 1.4430 |  |
| 16 | 1.4380 |  |
| 17 | 1.4345 |  |
| 18 | 1.4305 | kit 1 |
| 19 | 1.4330 |  |
| 20 | 1.4455 |  |
| 21 | 1.4360 |  |
| 22 | 1.4325 |  |
| 23 | 1.4425 |  |
| 24 | 1.4465 |  |
| 25 | 1.4475 |  |
| 26 | 1.4325 |  |
| 27 | 1.4420 |  |
| 28 | 1.4440 |  |
| 29 | 1.4315 |  |
| 30 | 1.4330 |  |

Two vials were selected for constitution. The vial having a diameter closest to or equal to 1.41 inches ("vial 1"), the lower end of the allowed SPI vial diameter had a measured diameter of 1.4305 inches. The vial having a diameter closest to or equal to 1.47 inches ("vial 2"), the upper end of the allowed SPI vial diameter, was measured to have a diameter of 1.4545 inches.

The selected kits were constituted as described above and tested for Vincristine Sulfate, Related Compounds and particle size and distribution following adapted Vincristine sulfate injection USP methods.

The two study kits were constituted using the above instructions, except that instead of the water bath, the Dri-Block heater was used with a block containing a 1.480 inch vial container hole. The block temperature was monitored by placing a thermometer into the block's thermometer hole which is situated in proximity to the vial container hole. The block heater was set to a temperature of 75° C. and allowed to heat until the block thermometer read 75±2° C. The heated block was then equilibrated for a minimum of 15 minutes (time recorded). The conditions are noted in Table 3. Each vial was then inserted into the 75±2° C. heated block for 14 minutes±15 seconds (time recorded), and then removed and allowed to come to ambient temperature by placing the vial in ambient conditions over about 60 minutes.

Time and block temperatures were recorded as indicated in Table 4 during constitution. Analytical results were recorded in Tables 5, 6 and 7.

TABLE 3

Dry Block Temperature Equilibration

|  | Time | Time between Successive Readings |
|---|---|---|
| Dry Block Set to 75° C. | 8:35 AM |  |
| First instance thermometer reads 75 ± 2° C. | 8:46 AM | 73.0° C. |
| 15 minute equilibration | 9:01 AM | 75.2° C. |

TABLE 4

Dry Block Constitution Parameters

| Vial ID | SPI Vial Diameter | Temperature T = 0 mins. 75 ± 1° C. | Temperature T = 1 mins. For info. | Temperature T = 5 mins. For info. | Temperature T = 14 mins. 75 ± 1° C. | Time at Removal 14 min ± 15 sec |
|---|---|---|---|---|---|---|
| 12 | 1.4545 | 75.2° C. | 74.5° C. | 73.2° C. | 74.2° C. | 9:24AM |
| 18 | 1.4305 | 75.2° C. | 74.6° C. | 73.2° C. | 74.3° C. | 10:02AM |

TABLE 5

Total & Free Vincristine Results

| Kit ID | Total Vincristine |
|---|---|
| Kit 1 | 102.10% |
| Kit 2 | 102.14% |

TABLE 6

Related Compounds Results

| Kit ID | N-Desformylvincristine | Any other compound |
|---|---|---|
| Kit 1 | 1.314 | 0.572 |
| Kit 2 | 1.345 | 0.574 |

TABLE 7

Particle Size Distribution

| Kit ID | Mean Diameter | $D_{25}$ | $D_{90}$ |
|---|---|---|---|
| Kit 1 | 108 nm | 90 nm | 139 nm |
| Kit 2 | 107 nm | 91 nm | 138 nm |

Results and Discussion

The constitution of VSLI was achieved using constitution vials having a diameter of 1.4305 and 1.4545 inches using the Dri-Block heater. These represented vials closest to the 1.41 inch lower limit and 1.47 inch upper limits allowed for vial diameters. During the 14 minute incubation of the VSLI vials in the heating block, the block temperature dropped no more than 1 degree due to temperature equilibration between the space gap between the block well diameter and either diameter of vials. This kinetics of the heat transfer did not affect the preparation of VSLI. After 14 minutes of exposure to the Dri-Block heat equilibrated at 75° C., the resulting constituted VSLI from both vials achieved greater than 97% vincristine encapsulation. The incubation using the Dri-Block resulted in an encapsulation efficiency averaging 2.175% free vincristine. No new or increased impurities were observed with the Dri-Block heating profile. The principle degradant, N-desformylvincrisine, was observed at an average of 1.33%, with no other impurity greater than 0.574%, and total impurities of no more than 3.10%. The particle size distribution was consistent with VSLI specifications with an average diameter of 107.5 nm diameter and mean $D_{25}$ of 90.5 nm and $D_{90}$ of 138.5 nm, VSLI prepared with Dri-Block heating released approximately 84 percent of the vincristine by 72 hours by IVR analysis.

In conclusion, VSLI constituted using the dry block heater equilibrated at 75±2° with an incubation period of 14 minutes±15 seconds encapsulated greater than 99% of vincristine in the sphingomyelin-cholesterol liposomes, and no anomalies were recorded during this experiment. The data establish a dry block constitution temperature profile that leads to a product that efficiently encapsulates vincristine and demonstrates that the dry block heater can be substituted for a water bath in the constitution of VSLI.

Example 3

In this study the levels of vincristine degradant products were measured to provide a range of constitution time using the dry block procedure.

Equipment and Materials

Dri-Block® equipped with 1.476" (±0.004) diameter well and thermometer pocket.

Thermometer with a diameter no greater than 7 mm, and accurate to ±1° C. in the range of 0°-100° C.
Calibrated stopwatch or timer
Margibo® Kits, Lot # TTX0611 (Talon Therapeutics, Inc.)

Procedure

Three Marqibo® Kits were selected at random and constituted by heating in the dry block at three different times (13, 14 and 15 minutes, respectively) at 75° C. The constituted vials were tested for Total and Free Vincristine Sulfate, Related Compounds, particle size and distribution using adapted vincristine sulfate Injection USP methods.

The study kits were constituted using the instructions as described above except that, instead of a water bath, the Dri-Block® heater was used with a block containing a 1.476 inch (±0.004") vial container hole. The block temperature was monitored by placing a thermometer into the block's thermometer hole which is situated in proximity to the vial container hole. The block was set to a temperature of 75° C. and allowed to heat until the thermometer in the block reads 75±2° C. The heated block was then equilibrated for a minimum of 15 minutes. The conditions were recorded in Table 9. Each vial was then inserted into the 75±2° C. heated block for 13 minutes±15 seconds, 14 minutes±15 seconds, and 15 minutes±15 seconds, respectively. The vials were then removed and placed at ambient temperature. The constituted vials were allowed to cool at ambient temperature for at least 60 minutes prior to testing.

Time and block temperatures were recorded as indicated in Tables 9 and 10 during constitution. Analytical results were recorded in Tables 11, 12 and 13.

TABLE 9a

Dry Block Temperature Equilibration (Vial 1)

| | Time | Time between Successive Readings |
|---|---|---|
| Dry Block Set to 75° C. | 8:20 AM | |
| First instance Thermometer reads 75 ± 2° C. | 8:48 AM | NA |
| 15 minute equilibration* | 9:03 AM | 15 mins. |

*Temperature at end of 15 minute equilibration period: 75.2° C.

TABLE 9b

Dry Block Temperature Equilibration (Vial 2)

| | Time | Time between Successive Readings |
|---|---|---|
| Dry Block Set to 75° C. | 9:17 AM | |
| First instance Thermometer reads 75 ± 2° C. | 9:17 AM | NA |
| 15 minute equilibration* | 9:32 AM | 15 mins. |

*Temperature at end of 15 minute equilibration period: 75.2° C.

TABLE 9c

Dry Block Temperature Equilibration (Vial 2)

| | Time | Time between Successive Readings |
|---|---|---|
| Dry Block Set to 75° C. | 9:47 AM | |
| First instance Thermometer reads 75 ± 2° C. | 9:47 AM | NA |
| 15 minute equilibration* | 10:02 AM | 15 mins. |

*Temperature at end of 15 minute equilibration period: 75.1° C.

TABLE 10

Dry Block Constitution Parameters

| Vial | SPI Vial Diameter | Temp T = 0 75 ± 1° C. | Temp T = 1 mins. For info. | Temp T = 5 mins. For info. | Temp T = 13 mins. ±15 secs. | Temp T = 14 mins. ±15 secs. | Temp T = 15 mins. ±15 secs. |
|---|---|---|---|---|---|---|---|
| 1 | 1.4490 | 75.2° C. | 74.6° C. | 73.2° C. | 74.2° C. | | |
| 2 | 1.4360 | 75.2° C. | 74.5° C. | 73.2° C. | | 74.1° C. | |
| 3 | 1.4355 | 75.2° C. | 74.6° C. | 73.3° C. | | | 74.2° C. |

TABLE 11

Total & Free Vincristine Results

| Kit ID | Total Vincristine |
|---|---|
| Kit 1 | 100.91 |
| Kit 2 | 100.59 |
| Kit 3 | 100.43 |

TABLE 12

Related Compounds Results

| Kit ID | N-Desformylvincristine | Any other compound |
|---|---|---|
| Kit 1 | 1.498 | 0.590 |
| Kit 2 | 1.506 | 0.587 |
| Kit 3 | 1.464 | 0.593 |

TABLE 13

Particle Size Distribution

| Kit ID | Mean Diameter | $D_{25}$ | $D_{90}$ |
|---|---|---|---|
| Kit 1 | 107 nm | 91 nm | 137 nm |
| Kit 2 | 106 nm | 90 nm | 137 nm |
| Kit 3 | 107 nm | 90 nm | 138 nm |

Results and Discussion

One constituted kit each was placed in an equilibrated heat block at 75° C. for 13, 14 and 15 minutes respectively. All the sample times produced encapsulated vincristine, and there were no significant differences in test results noted between the three vials. Greater than 97% vincristine encapsulation was observed with all three vials using the Dri-Block resulting in an encapsulation efficiency with a maximum 2.3% free vincristine. No new or increased impurities were observed with the Dri-Block heating profile. The principal degradant, N-desformylvincrisine, was observed at a maximum of 1.51% with no other impurity greater than 0.59% and total impurities of no more than 3.3%. The particle size distribution was consistent with VSLI specifications with an average diameter of 107 nm diameter and mean $D_{25}$ of 90 nm and $D_{90}$ of 137 nm.

In conclusion, VSLI constituted with the substitution of the water bath with a Dri-Block equilibrated at 75±2° C. with an incubation period of 13 to 15 minutes (±15 seconds) encapsulated vincristine efficiently and no anomalies were recorded during the conduct of the experiment. The data establishes a Dri-Block constitution temperature profile that leads to efficient VSLI constitution and shows that the Dri-block heater can be substituted for a water bath in the constitution of the VSLI.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:

1. A method of preparing a pharmaceutically acceptable liquid composition comprising liposome-encapsulated vincristine which is free of substantial degradation products, the method comprising:
   (a) constituting in a single vial (i) a first solution comprising vincristine sulfate at a concentration of about 1 mg/ml to about 5 mg/ml, wherein the first solution has a pH of about 3.5 to about 5.5; and (ii) a second solution comprising sphingomyelin/cholesterol liposomes at a low pH;
   (b) raising the pH of the constituting solution in the single vial to a pH of about 7.0 to 7.5;
   (c) heating the single vial comprising the constituting solution in a dry heat block equilibrated at about 75° C. for at least about 13 to about 18 minutes, wherein said heat block comprises one or more bores about 1-5% larger than the average length or diameter of the single vial to produce a solution comprising constituted liposome encapsulated vincristine; and
   (d) equilibrating the constituted solution to room temperature.

2. The method of claim 1, wherein the pH of the second solution comprising the liposomes is about 4.0.

3. The method of claim 2, wherein the second solution further comprises a citrate buffer.

4. The method of claim 1, wherein the pH of the constituting solution is raised by the addition of a third solution comprising a buffer at a pH of about 9.0.

5. The method of claim 4, wherein the third solution comprises sodium phosphate buffer.

6. The method of claim 1, wherein the constituting solution comprises a concentration of about 0.1/1.0 to about 0.2/2.0 vincristine sulfate to lipid.

7. The method of claim 6, wherein the concentration of vincristine sulfate in the constituted solution is about 0.1 mg/mL to about 0.5 mg/mL.

8. The method of claim 7, wherein the concentration of vincristine sulfate in the constituted solution is about at about 0.15 mg/mL to about 0.2 mg/mL.

9. The method of claim 4, wherein the first solution comprises vincristine sulfate USP (5 mg/5 mL), which is equivalent to 4.5 mg/5 mL vincristine free base, and 500 mg/5 mL mannitol, the second solution comprises sphingomyelin/cholesterol liposomes consisting of 73.5 mg/mL sphingomyelin, 29.5 mg/mL cholesterol, 33.6 mg/mL citric acid, 35.4 mg/mL sodium citrate, and the third solution comprises 355 mg/25 mL dibasic sodium phosphate and 225 mg/25 mL sodium chloride.

10. The method of claim 1, wherein the ratio of sphingomyelin to cholesterol in the liposome is between about 75/25 mol %/mol % sphingomyelin/cholesterol to 30/50 mol %/mol % sphingomyelin/cholesterol.

11. The method of claim 1, wherein the liposomes have a size range of about 0.05-0.5 microns.

12. A method of treatment comprising administering the liposome-encapsulated vincristine made by the method of claim 1, wherein a patient with cancer is administered the liposome encapsulated vincristine at a dose of about 1.5 to about 2.4 mg/m$^2$.

13. The method of claim 12, wherein the cancer is selected from the group consisting of lymphoma, leukemia, myeloma, brain cancer and neuroblastoma.

14. The use of claim 12, wherein the pharmaceutically acceptable liquid composition comprising liposome-encapsulated vincristine is administered by intravenous infusion over a period of about 30 to 60 minutes.

15. The method of claim 12, wherein the pharmaceutically acceptable liquid composition comprising liposome-encapsulated vincristine is administered by intravenous infusion once every 7-28 days.

* * * * *